US012310627B1

(12) United States Patent
Condon

(10) Patent No.: US 12,310,627 B1
(45) Date of Patent: May 27, 2025

(54) EXTERNAL FIXATION DEVICE

(71) Applicant: Christopher Condon, Henderson, NV (US)

(72) Inventor: Christopher Condon, Henderson, NV (US)

( * ) Notice: Subject to any disclaimer, the term of this patent is extended or adjusted under 35 U.S.C. 154(b) by 138 days.

(21) Appl. No.: 18/084,698

(22) Filed: Dec. 20, 2022

Related U.S. Application Data

(63) Continuation-in-part of application No. 17/084,158, filed on Oct. 29, 2020, now abandoned, which is a continuation-in-part of application No. 16/818,240, filed on Mar. 13, 2020, now abandoned.

(60) Provisional application No. 62/819,076, filed on Mar. 15, 2019.

(51) Int. Cl.
*A61B 17/62* (2006.01)
*A61B 17/64* (2006.01)
*A61B 17/66* (2006.01)

(52) U.S. Cl.
CPC .......... *A61B 17/66* (2013.01); *A61B 17/6425* (2013.01)

(58) Field of Classification Search
CPC ..... A61B 17/62; A61B 17/64; A61B 17/6416; A61B 17/6425; A61B 17/6441; A61B 17/645; A61B 17/6466; A61B 17/66; A61B 17/606
USPC ...................................... 606/53–59
See application file for complete search history.

(56) References Cited

U.S. PATENT DOCUMENTS

| | | | | |
|---|---|---|---|---|
| 5,393,161 A * | 2/1995 | Mata | ................... | A61B 17/6416 403/112 |
| 6,030,386 A * | 2/2000 | Taylor | ................... | A61B 17/62 606/56 |
| 8,257,353 B2 * | 9/2012 | Wong | ................... | A61B 17/6416 606/59 |
| 10,082,384 B1 * | 9/2018 | Singh | ................... | A61B 34/10 |
| 10,390,859 B2 * | 8/2019 | Sakkers | ................... | A61B 17/62 |
| 2009/0198235 A1 * | 8/2009 | Steiner | ................... | A61B 17/62 606/57 |

(Continued)

FOREIGN PATENT DOCUMENTS

| | | | | |
|---|---|---|---|---|
| DE | 3802743 A1 * | 8/1989 | ............. | A61B 17/62 |
| WO | WO-9106253 A1 * | 5/1991 | ............. | A61B 17/62 |
| WO | WO-0115611 A1 * | 3/2001 | ............. | A61B 17/62 |

OTHER PUBLICATIONS

Machine translation of DE 3802743 A1. (Year: 1989).*
Machine translation of WO 9106253 A1. (Year: 1991).*

*Primary Examiner* — Eduardo C Robert
*Assistant Examiner* — David C Comstock
(74) *Attorney, Agent, or Firm* — John Rizvi; John Rizvi, P.A.—The Patent Professor ®

(57) ABSTRACT

An external fixation device for stabilizing fractured bones in the treatment of traumatic injuries may include a lower support. An upper support may be disposed in spaced-apart relationship to the lower support. At least one elongated link or connector may connect the upper support to the lower support. A pivotal base joint may pivotally connect each connector to the lower support. A ball-and-socket joint may swivably connect the upper support to the at least one connector. The lower support and the upper support may be attached to bones on opposite sides of a fracture site. The lower and upper supports remain exterior to the limb of the patient to facilitate periodic adjustments of the lower support (Continued)

and/or the upper support relative to the connectors to achieve a selected clinical outcome.

5 Claims, 22 Drawing Sheets

(56) References Cited

U.S. PATENT DOCUMENTS

| | | | | |
|---|---|---|---|---|
| 2014/0135764 | A1* | 5/2014 | Ross | A61F 5/042 606/57 |
| 2017/0354439 | A1* | 12/2017 | Mannanal | A61B 17/62 |
| 2018/0368887 | A1* | 12/2018 | Lauf | A61B 17/62 |

* cited by examiner

EXTERNAL FIXATION DEVICE

CROSS-REFERENCE TO RELATED APPLICATION

This application is a Continuation-In-Part (CIP) of U.S. Non-Provisional patent application Ser. No. 17/084,158, filed on Oct. 29, 2020, which is a Continuation-In-Part (CIP) of U.S. Non-Provisional patent application Ser. No. 16/818,240, filed on Mar. 13, 2020, which in turn claims the benefit of U.S. Provisional Patent Application No. 62/819,076, filed on Mar. 15, 2019, all of which are incorporated by reference herein in their entirety.

FIELD OF THE INVENTION

The present invention relates generally to orthopedic fixation devices, and more particularly, to an external fixation device which is simple in design and installation, and aligns and stabilizes fractured bones in the treatment of traumatic injuries.

BACKGROUND OF THE INVENTION

The human skeleton includes 206 bones which provide a protective framework for internal organs as well as lever structures for the arms and legs. Bones may also provide a reservoir for calcium and other minerals as well as contain bone marrow for the formation of blood cells. Bones frequently are deformed as a result of genetic abnormality or may become injured through use, particularly in the case of athletes. Fractured and broken bones must be repaired promptly in order to restore optimal functioning of the bones.

The field of orthopedics in medicine seeks to facilitate healing of bones in the event of deformity or injury. To this end, fixation devices may be applied to the deformed or injured bone to straighten or stabilize the bone as it heals. Some types of fixation devices may be used to gradually adjust the orientation and/or spacing of bone segments on opposite sides of a repair site.

Orthopedic fixation devices may take many forms depending on the nature, location and severity of the fracture. Fixation devices may include rods, screws, plates and other mechanical components which apply corrective forces to the bone in the area of the bone fracture. Some fixation devices may be internal, or placed inside the body of the patient, whereas other fixation devices may be external to the body. Internal fixation devices may be permanently-installed to apply static corrective forces to the bone. External fixation devices, on the other hand, may be used to apply dynamic corrective forces to the bone over a period of time by the application of a wrench or other tool to the device for gradual adjustment of the device.

Conventional external fixation devices may have various limitations such as the inability to pivot for adjustment of the devices. Some external fixation devices may be complicated in design and difficult to install. Conventional external fixation devices may also positionally interfere with a hand, foot or other body part of the patient.

Accordingly, there is an established need for an external fixation device which solves at least one of the aforementioned problems. For example, there remains a need for an external fixation device that is simple in design and installation and aligns and stabilizes fractured bones in the treatment of traumatic injuries.

SUMMARY OF THE INVENTION

The present invention is directed to an external fixation device which is simple in design and installation and aligns and stabilizes fractured bones in the treatment of traumatic injuries. An illustrative embodiment of the external fixation device may include a first support and a second support. At least one connector may connect the first support to the second support. Each connector may be pivotably attached to the first and second supports, such as via a pivotal base joint and/or a ball-and-socket joint. The bone may be attached to the first support and the second support across a fracture site through bolts which extend from the bone to the corresponding first support and second support outside the patient. Accordingly, the first support and the second support may be pivotally adjustable with respect to each other to facilitate, for instance, static or dynamic compressions or lengthening of the tibia or tibial shaft for ankle fusion, offloading or keeping a patient off a foot ulcer or wound, for example. With the ball-and-socket joint angulation, the device may work around the foot of the patient instead of the foot working around the device. This expedient may facilitate more robust angulation in the correction of fracture sites and may result in a more predictable clinical outcome.

Introducing an illustrative embodiment of the invention, the present invention includes an external fixation device which is simple in design and installation and aligns and stabilizes fractured bones in the treatment of traumatic injuries, comprising:

a first support configured to extend at least partially around a limb;

a second support configured to extend at least partially around said limb, and disposed in spaced-apart relationship to the first support; and one or more connectors, wherein each connector is pivotably connected to the first support by a first articulated connection and is pivotably connected to the second support by a second articulated connection.

In a second aspect, at least one of the first articulated connection and the second articulated connection may include a universal joint.

In another aspect, at least one of the first articulated connection and the second articulated connection may include a ball-and-socket joint.

In another aspect, freedom of rotation of a ball of the ball-and-socket joint relative to a socket of the ball-and-socket joint may be selectively adjustable.

In another aspect, a ball of the ball-and-socket joint may be removably received within a socket of the ball-and-socket joint.

In yet another aspect, a ball of the ball-and-socket joint may be carried by the connector.

In another aspect, each connector may be disconnectably connected to at least one of the first support and the second support.

In another aspect, each connector may be selectively connectable to different discrete positions along the first support such that a position of the first articulated connection along the first support may be varied.

In another aspect, the first support may include a plurality of fastener openings formed in discrete, spaced-apart positions along the first support for selective attachment thereto of said each connector.

In yet another aspect, each connector may be selectively connectable to different discrete positions along the second support such that a position of the second articulated connection along the second support may be varied.

In another aspect, the second support may include a plurality of fastener openings formed in discrete, spaced-apart positions along the second support for selective attachment thereto of said each connector.

In another aspect, at least one of the first and second supports may be C-shaped and configured to extend partially around a limb.

In another aspect, at least one of the first and second supports may be ring-shaped and configured to extend entirely around a limb.

In yet another aspect, at least one connector of the one or more connectors may be length-adjustable.

In another aspect, the length-adjustable connector may include a spacer assembly having a rod and at least one sleeve axially adjustable relative to the rod.

In another aspect, each connector of the one or more connectors may be length-adjustable.

In another aspect, the one or more connectors may consist of three connectors.

In yet another aspect, the one or more connectors may consist of four connectors.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward an external fixation device which is simple in design and installation and aligns and stabilizes fractured bones in the treatment of traumatic injuries.

Figure 1:
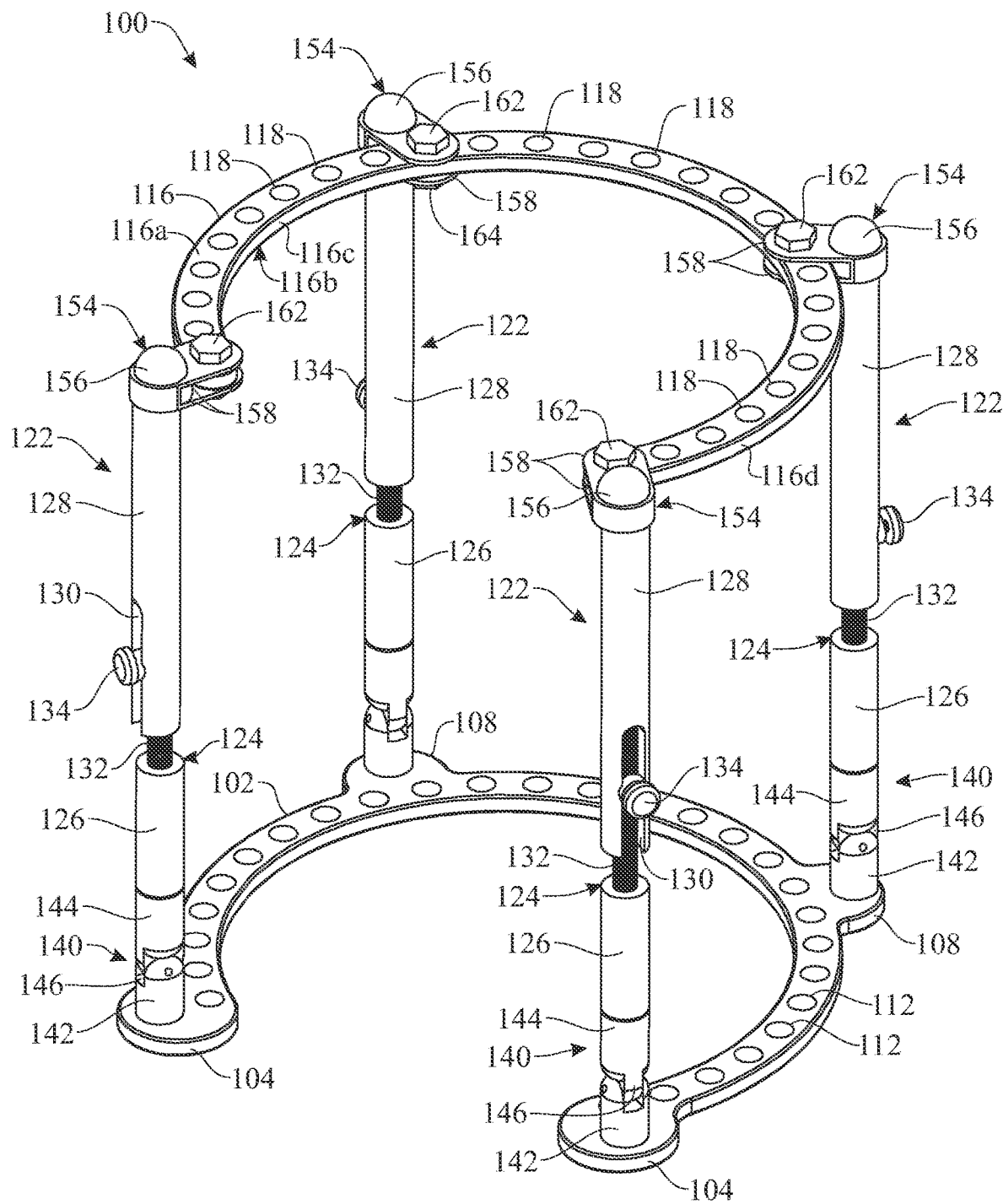
FIG. 1 presents a top perspective view of an external fixation device in accordance with an illustrative embodiment of the present invention, the external fixation device shown assembled and including four connectors extending between the upper and lower supports.

Referring initially to FIGS. 1-8, an illustrative embodiment of the external fixation device is generally indicated by reference numeral 100. As shown in FIG. 1, the external fixation device 100 may include a first or lower support 102. A second or upper support 116 may be disposed in spaced-apart relationship to the lower support 102. At least one elongated link or connector 122 may connect the upper support 116 to the lower support 102. As will be described hereinafter, each connector 122 is elongated, length-adjustable and generally rigid to torsion. In some embodiments, a plurality of connectors 122 may connect the upper support 116 to the lower support 102, as illustrated. A pivotal base joint 140 may pivotally attach each connector 122 to the lower support 102. A ball-and-socket joint 154 may swivably attach the upper support 116 to each corresponding connector 122. Accordingly, by pivoting the lower support 102 and adjusting the position of the upper support 116 relative to the connectors 122, various orientations of the upper support 116 relative to the lower support 102 may be achieved to attain different fixation procedures depending typically on the nature, location and severity of a bone fracture.

The various components of the external fixation device 100 may be fabricated of metal (e.g., aluminum), plastic such as, but not limited to, DELRIN® plastic, polymers (e.g., nylon), composites, or combinations thereof. These materials should be understood as non-limiting examples.

Figure 3:
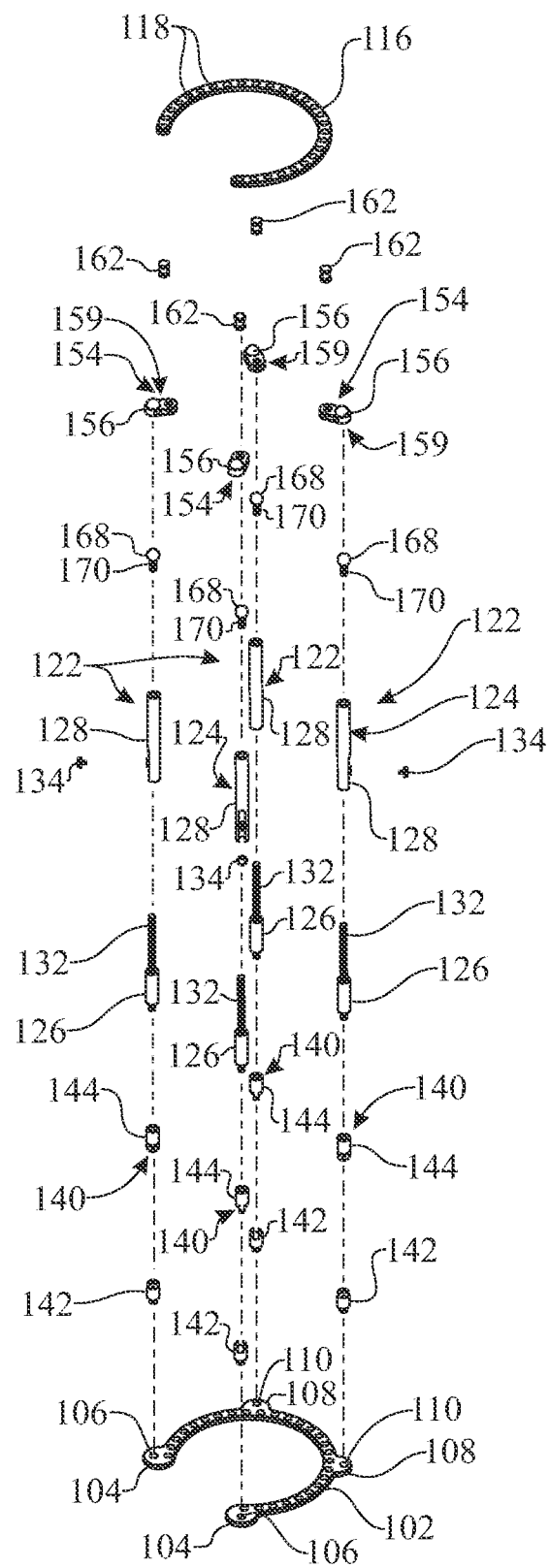
FIG. 3 presents an exploded top perspective view of the external fixation device of FIG. 1.

With continued reference to FIG. 1, in some embodiments, such as the present embodiment, the lower support 102 and the upper support 116 may each have a C-shaped configuration. The lower support 102 may have a pair of spaced-apart widened ends or terminal flanges 104. As shown in FIG. 3, an opening 106 may extend through each terminal flange 104. As best shown in FIG. 1, a plurality of spaced-apart fastener openings 112 may extend through the lower support 102 between the terminal flanges 104. A pair of spaced-apart intermediate protrusions or flanges 108 may extend from the lower support 102 between the terminal flanges 104. As illustrated in FIG. 3, an opening 110 may extend through each intermediate flange 108. A plurality of spaced-apart fastener openings 118 may extend through the upper support 116 for purposes which will be hereinafter described. The fastener openings 118 in the upper support 116 may correspond in number and position to the respective fastener openings 112 in the lower support 102. Each of the openings 106 in the terminal flanges 104, the openings 110 in the intermediate flanges 108, the fastener openings 112 in the lower support 102 and the fastener openings 118 in the upper support 116 may be interiorly threaded.

Figure 4:
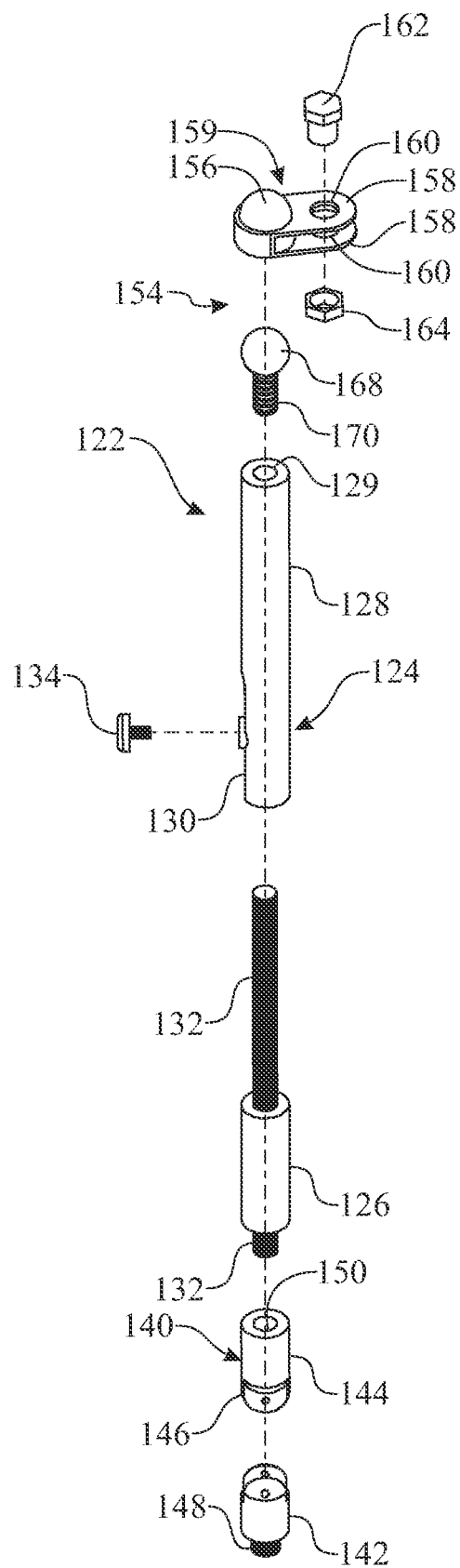
FIG. 4 presents an exploded top perspective view of one of the connectors of the external fixation device of FIG. 1.

In some embodiments, each connector 122 may be selectively adjustable in length, allowing a surgeon, doctor, nurse or other medical staff or user of the external fixation device 100 to adjust the length of the connectors 122 as required by medical treatment. For instance and without limitation, as best shown in FIGS. 1 and 4, in some embodiments, each connector 122 may include at least one spacer assembly 124 to allow length adjustment of the connector 122. The spacer assembly 124 may include a rod 132 which may be exteriorly threaded. A first or lower sleeve 126 may be threaded on or otherwise attached to the rod 132. A second or upper sleeve 128 may be threaded on the rod 132 above the lower sleeve 126. In the event that both the lower sleeve 126 and the upper sleeve 128 are threaded to the rod 132, the lower sleeve 126 and the upper sleeve 128 may be individually threaded or unthreaded along the rod 132 to adjust the separation between the lower sleeve 126 and the upper sleeve 128 and thereby achieve a selected length of each corresponding connector 122.

In some embodiments, an elongated slot 130 may be provided in the upper sleeve 128. A knob 134 may threadably engage the slot 130. When the upper sleeve 128 is fitted over or sleeved onto the rod 132, the knob 134 may be threaded through the slot 130 and tightened against the rod 132 to secure or reinforce the upper sleeve 128 at a selected position with respect to the rod 132. Though not shown herein, embodiments are contemplated in which the lower sleeve 126 may alternatively or additionally be provided with a similar slot and knob feature. In some embodiments, the upper sleeve 128 may have a length of about 150 mm and the rod 132 may have a length of about 200 mm.

Figure 2:
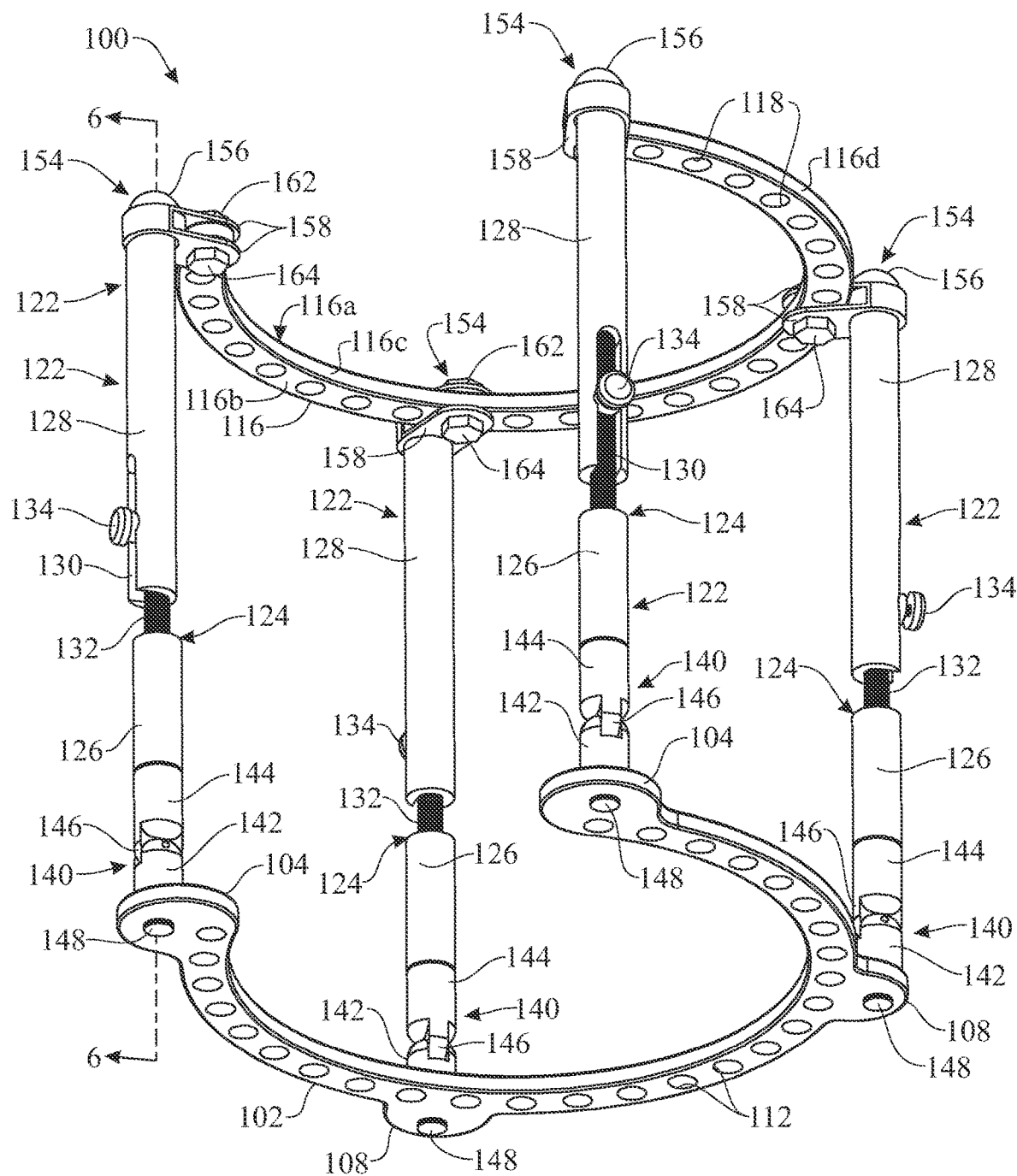
FIG. 2 presents a bottom perspective view of the external fixation device of FIG. 1, the external fixation device shown assembled.
Figure 6:
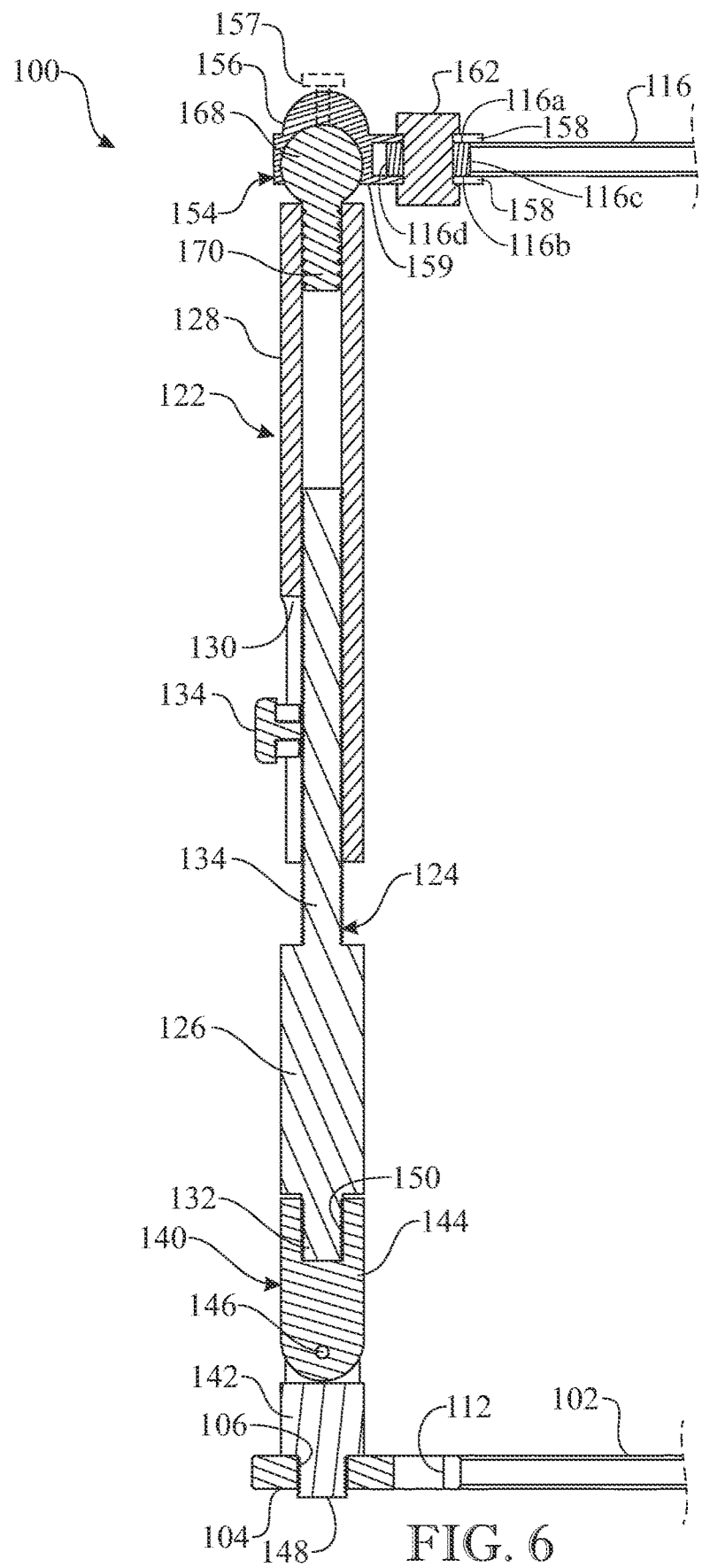
FIG. 6 presents a cross-sectional side elevation view, taken along section plane 6-6 indicated in FIG. 2, of a connector of the external fixation device of FIG. 1, with the upper support and the lower support disposed in axial alignment with each other and the plane of the lower support and the plane of the tipper support parallel to each other.

Referring again to FIG. 1, each pivotal base joint 140 may have any design which is suitable for the purpose of pivotally attaching the connector 122 to the lower support 102. For example, in some embodiments, each pivotal base joint 140 may include a lower joint component 142 which may be attached to the lower support 102 in a preferably disconnectable manner; for instance, as illustrated in FIGS. 2 and 6, a threaded joint shank 148 may extend from the lower joint component 142, and the joint shank 148 may be threaded into a corresponding one of the openings 106 in a terminal flange 104, as illustrated, or alternatively, into one of the fastener openings 112 of the lower support 102.

Furthermore, each pivotal base joint 140 may include an upper joint component 144 which may be attached to the connector 122 in a preferably disconnectable manner. For example, as best shown in FIG. 4, in some embodiments, the upper joint component 144 may have an interiorly-threaded opening 150 which may threadably receive a second or bottom threaded end of the rod 132 of the spacer assembly 124 adjacent to the lower sleeve 126. A joint hinge 146 may pivotally attach the upper joint component 144 to the lower joint component 142.

In turn, and with continued reference to FIG. 4, each ball-and-socket joint 154 may include a ball 168. A threaded shank 170 may extend from the ball 168. The threaded shank 170 may be threaded into a threaded opening 129 formed in the upper end of the upper sleeve 128 of the spacer assembly 124. A socket 156 may receive the ball 168. The ball 168 is movable in a universal or swivel motion inside the socket 156, the ball 168 and socket 156 forming a ball-joint mechanism.

Figure 5:
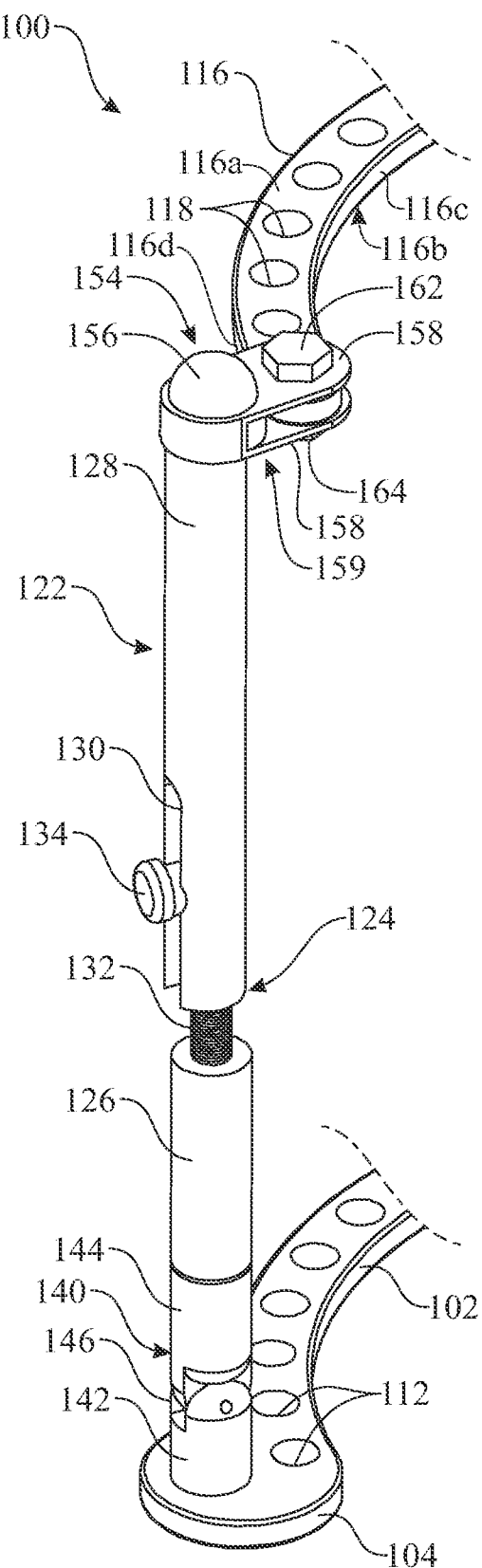
FIG. 5 presents an enlarged, perspective view of the connector of FIG. 4 secured to the upper and lower supports of the external fixation device of FIG. 1.

As further shown in FIG. 4, at least one protruding arm or flange 158 may extend from the socket 156. In some embodiments, a pair of parallel, spaced-apart protruding arms or flanges 158 may extend from the socket 156, as illustrated, the pair of flanges 158 forming a clamp assembly configured to clamp over and onto opposite, outer sides of the second support 116 at different positions along the upper support 116. More specifically, as best shown in FIGS. 5 and 6, the upper support 116 includes an outer, top side 116a, an outer, bottom side 116b arranged opposite to the top side 116a and facing the lower support 102, an inner lateral side 116c and an outer lateral side 116d; the pair of flanges 158 of the present embodiment are mounted over and onto the opposite, outer, top and bottom sides 116a and 116b of the upper support 116.

A pair of registering fastener openings 160 may extend through the flanges 158. A threaded, clamp fastener 162 may be extended through the aligned fastener openings 160 in the flanges 158 and through a selected one of the registering fastener openings 118 in the upper support 116, and a securing nut 164 may be threaded on the clamp fastener 162 to attach the flanges 158, and therefore the socket 156, to the upper support 116. In some embodiments, a ball joint fastener 157 (shown in phantom lines in FIG. 6) may be threaded into the socket 156 from outside the socket 156 (e.g., from outside a top area of the socket 156) to press against the ball 168, thereby facilitating selective tightening of the ball-and-socket joint 154 by preventing swivel or rotation of the ball 168 relative to the socket 156 and thereby lock the ball-and-socket joint 154 in place. As shown, the flanges 158 and socket 156 form a connecting member 159, or connector, which interfaces between the connector 122 and the tipper support 116 to articulately connect one to the other at different selectable positions along the upper support 116.

Figure 7:
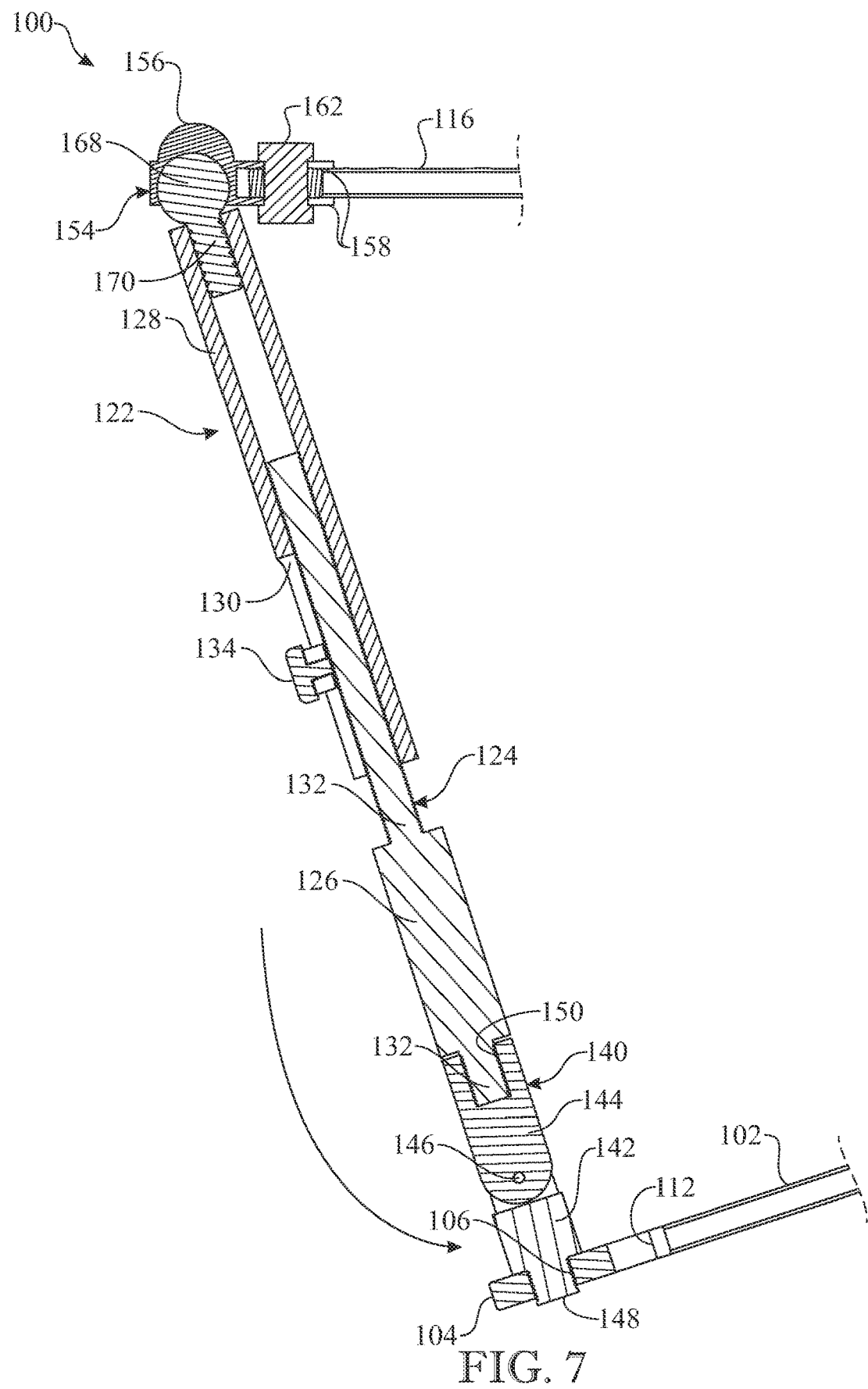
FIG. 7 presents a cross-sectional side elevation view of the connector of FIG. 6, with the upper support and the lower support disposed in axial misalignment with each other and the plane of the lower support and the plane of the upper support in angular relationship to each other.
Figure 8:
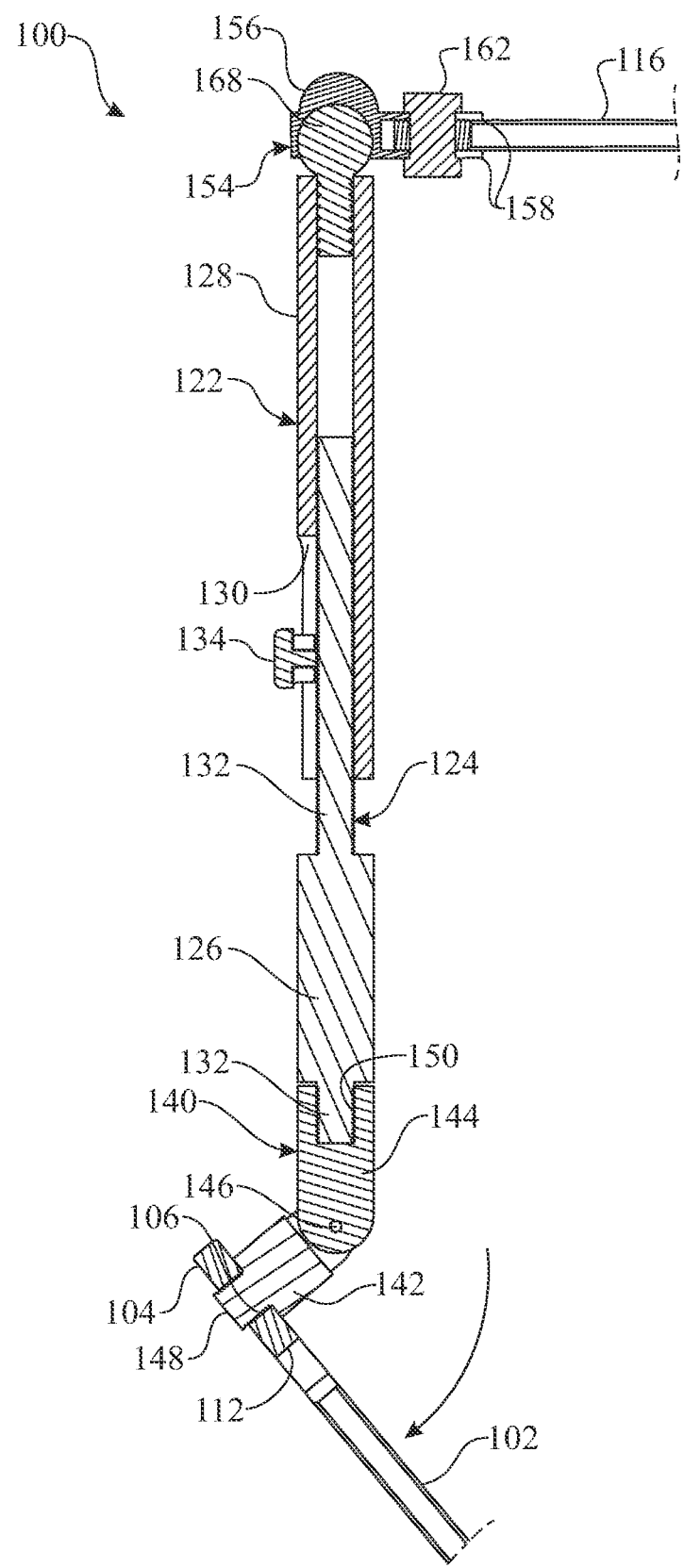
FIG. 8 presents a cross-sectional side elevation view of the connector of FIG. 6, with the lower support pivoted away from the connector.
Figure 9:
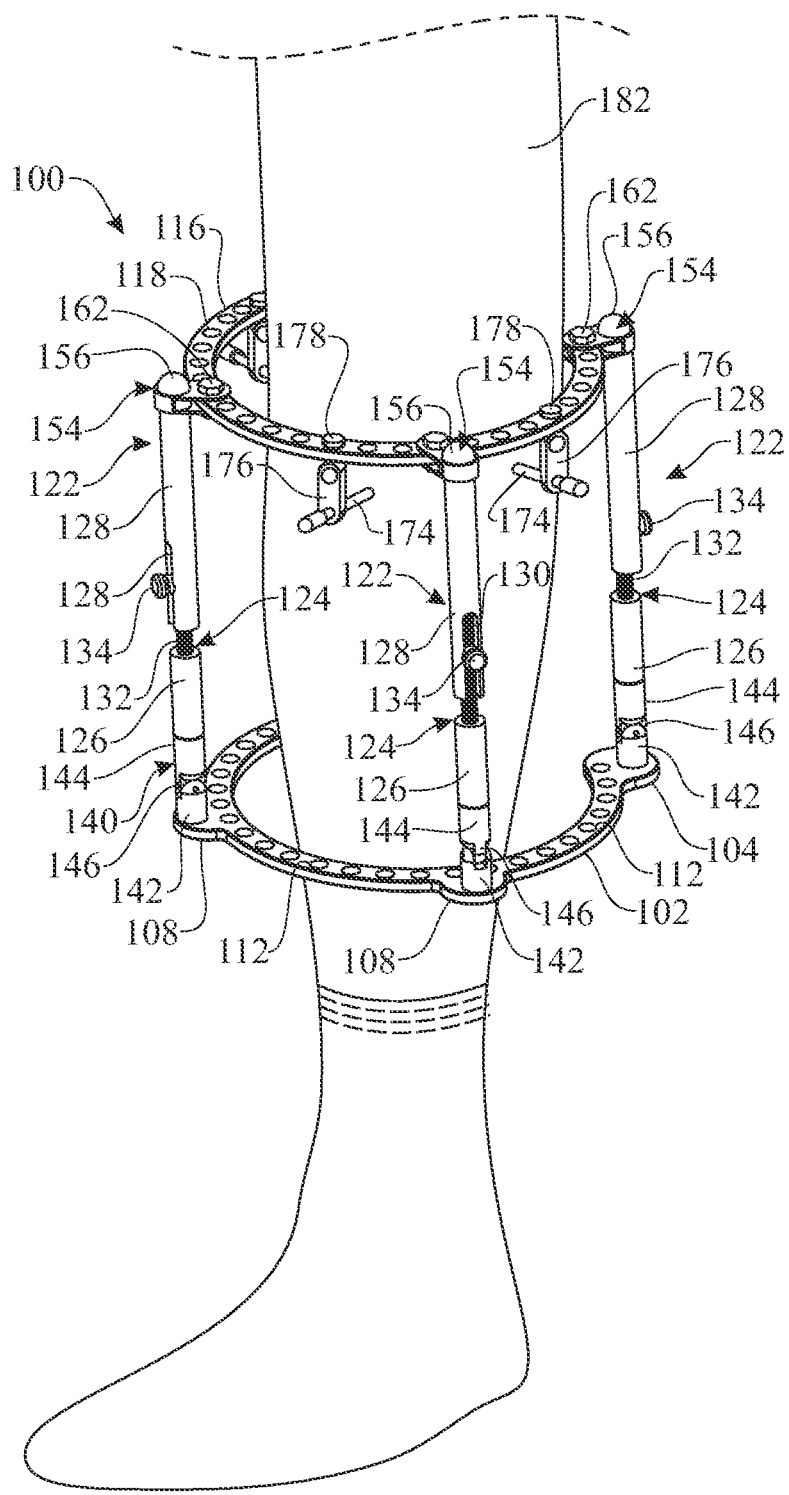
FIG. 9 presents a top perspective view of the external fixation device of FIG. 1 deployed in place on the leg of a patient in an illustrative application of the external fixation device.

Referring next to FIGS. 5-9, and initially to FIG. 9, in an illustrative application of the external fixation device of the present disclosure, the external fixation device 100 may be installed in the leg 182 of a patient to stabilize and maintain the leg 182 in alignment as the leg 182 heals of a fracture resulting from a traumatic injury. In some applications, the external fixation device 100 may be installed on the patient's leg 182 to carry out static or dynamic compressions or lengthening of the tibia or tibial shaft for correction, ankle fusion or offloading or to keep the patient off a foot ulcer or wound as the ulcer or wound heals.

The external fixation device 100 may be assembled by attaching the elongated links or connectors 122 to the lower support 102 and tipper support 116. For example, the connectors 122 may be attached to the respective terminal flanges 104 and intermediate flanges 108 on the lower support 102, as shown in FIG. 1. The connectors 122 may be attached to the lower support 102 typically by threading the joint shank 148 on the lower joint components 142 of the pivotal base joints 140 into the openings 106 of the terminal flanges 104 and into the openings 110 of the intermediate flanges 108. Each lower sleeve 126 may be threaded on the respective rod 132 of the corresponding spacer assembly 124, and the lower end of the rod 132 may be threaded into the opening 150 in the upper joint component 144 of the pivotal base joint 140. The upper sleeve 128 may be threaded onto the rod 132 and the knob 134 threaded through the slot 130 and against the rod 132 to complete the spacer assembly 124.

In some embodiments, the ball-and-socket joints 154 may come pre-assembled. In other embodiments, each ball-and-socket joint 154 may be assembled by threading the shank 170 into the opening 129 of the upper sleeve 128 and snap-fitting the socket 156 over the ball 168. The flanges 158 may receive the upper support 116. The clamp fastener 162 may then be extended through the aligned fastener openings 160 in the flanges 158 and through a selected registering one of the fastener openings 118 in the upper support 116, and the nut 164 may be threaded onto the clamp fastener 162 thereby securing the ball-and-socket joint 154 to the tipper support 116 while enabling ball-joint pivotal movement of the ball-and-socket joint 154.

The external fixation device 100 may be installed under general anesthetic by an orthopedic surgeon. Holes may initially be drilled into the undamaged areas of the bone on both sides of the fracture site (not illustrated). With reference to FIG. 9, fixation bolts 174 may be threaded into the drilled holes and extended out from the leg 182 of the patient. Fixation bolt brackets 176 may be used to attach the lower support 102 and/or the upper support 116 to the fixation bolts 174. Mount fasteners 178 may be extended through the fastener openings 112 of the lower support 102 and/or the fastener openings 118 of the upper support 116 to secure the fixation bolt brackets 176 to the corresponding lower support 102 or upper support 116. The elongated links or connectors 122 may be individually adjusted in length, as deemed necessary, typically by threading the lower sleeve 126 and the upper sleeve 128 on the rod 132 of the spacer assembly 124 in order to adjust the separation between the lower and upper sleeves 126 and 128. Adjustments may be made to the ball-and-socket joints 154 at the top end of the connectors 122 to ensure that the bone is aligned properly with little, if any, shortening of the bone.

As illustrated in FIGS. 5 and 6, the lower support 102 and the upper support 116 may be selectively and individually oriented such that the plane of each is oriented perpendicular to the longitudinal axis of each connector 122. Alternatively, as illustrated in FIGS. 7 and 8, the lower support 102 and the upper support 116 may be individually adjusted such that the plane of either or both is oriented at an acute angle (FIG. 7) or an obtuse angle (FIG. 8) with respect to the longitudinal axis of one or more of the connectors 122. This expedient may facilitate different configurations of the external fixation device 100 depending typically on the nature, location and severity of the bone fracture. Moreover, the positions or orientations of the lower support 102 and the upper support 116 relative to the connectors 122, as well as the length of the connectors 122, may be periodically adjusted throughout the course of treatment to achieve a desired clinical outcome.

It will be appreciated by those skilled in the art that the external fixation device 100 can be quickly and easily installed. With the angulation provided by the ball-and-socket joints 154, the external fixation device 100 will work around the foot of the patient instead of the patient's foot working around the external fixation device 100. This expedient may allow for a more robust angulation in the correction of fracture sites and may facilitate achievement of a more predictable clinical outcome. With reference to FIG. 9, the lower support 102 can be connected to the connectors 122 at any of the fastener openings 112 and the upper support 116 can be attached to the connectors 122 at any of the fastener openings 118 to achieve adjustability in the configuration of the external fixation device 100 depending on the particular application. Similarly, the fixation brackets 176 may be connected to the upper support 116 or lower support 102 at any of the fastener openings 118 or fastener openings 112, respectively, to adjustably position the fixation bolts 174 in dependence of the specific position of the fracture site.

Figure 10:
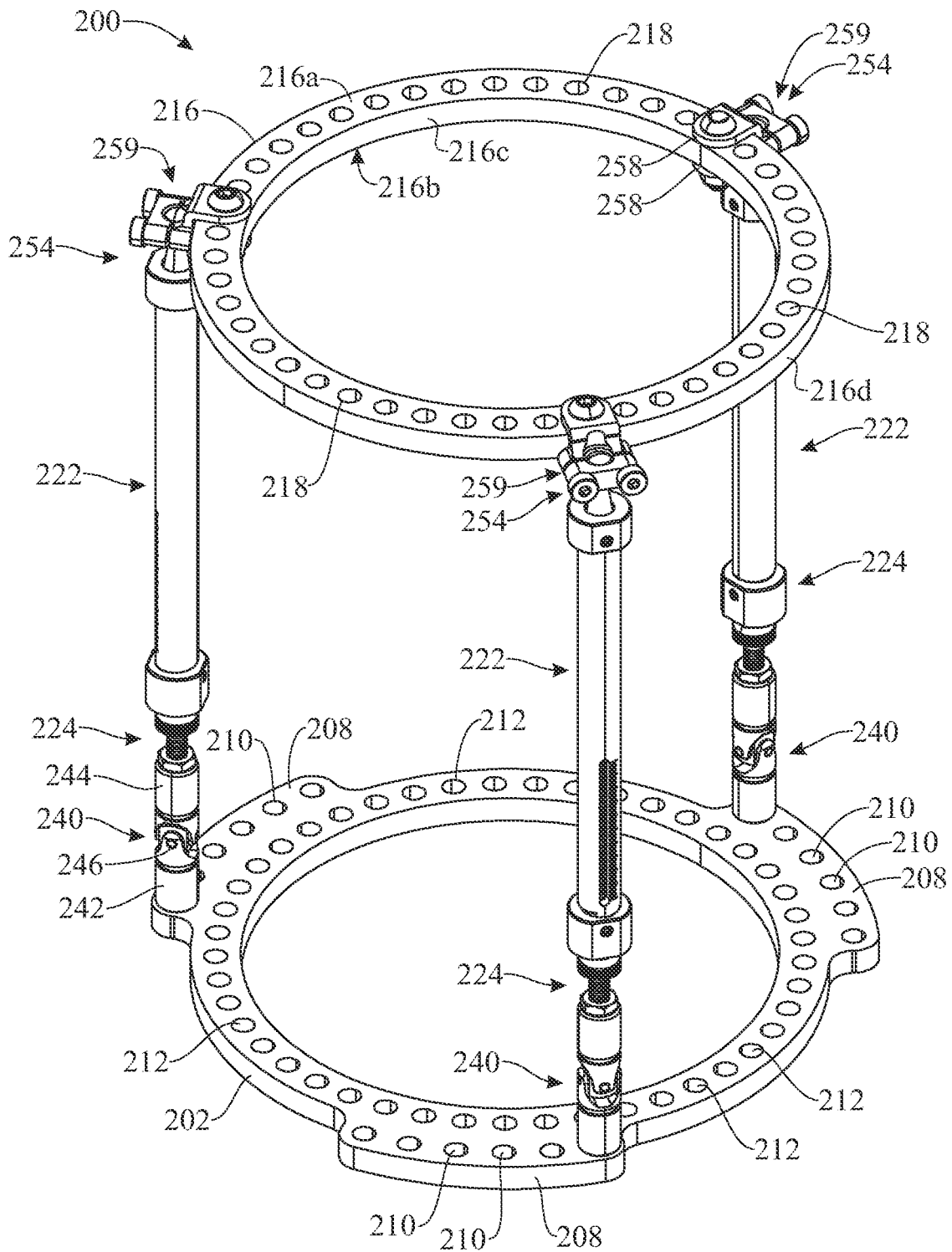
FIG. 10 presents a top perspective view of an external fixation device in accordance with a second illustrative embodiment of the present invention, the external fixation device shown assembled and including three connectors extending between annular tipper and lower supports.

Referring now to FIGS. 10-18, a second illustrative embodiment of the external fixation device is generally indicated by reference numeral 200. As shown in FIG. 10, similarly to the previous embodiment, the external fixation device 200 of the present embodiment includes a first or lower support 202 and a second or tipper support 216 in spaced-apart relationship with one another, and one or more elongated links or connectors 222 connecting the upper support 216 to the lower support 202. More specifically, as in the previous embodiment, a plurality of connectors 222 may connect the upper support 216 to the lower support 202; for example, in this specific embodiment, the external fixation device 200 includes three connectors 222. Similarly to the previous embodiment, each connector 222 is elongated, length-adjustable and generally rigid to torsion, and is attached to the lower support 202 and the upper support 216 by a respective articulated connection, and more specifically, by a pivotal base joint 240 and a ball-and-socket joint 254, respectively. Various orientations of the upper support 216 relative to the lower support 202 may be achieved by pivoting the lower support 202 and the upper support 216 relative to the connectors 222. Also similarly to the previous embodiment, the various components of the external fixation device 200 may be fabricated of metal, plastic such as, but not limited to, DELRIN® plastic, composites, or combinations thereof, for instance and without limitation.

As shown in FIG. 10, the lower support 202 and the upper support 216 of the present embodiment are formed as closed-looped bodies, which are preferably annular or ring-shaped. Similarly to the previous embodiment, a plurality of spaced-apart fastener openings 218 may extend through the upper support 216. In turn, the lower support 202 includes a plurality of spaced-apart fastener openings 212 arranged in discrete positions along a first circumference having a first radius about a center of the annular lower support 202, and a second plurality of spaced-apart fastener openings 210 arranged in discrete positions along a second circumference concentric to the first circumference and having a second radius lager than the first radius. The fastener openings 218 in the upper support 216 may correspond in number and position to the fastener openings 212 in the lower support 202. The fastener openings 210, 212 and 218 may be interiorly threaded. In the present embodiment, the fastener openings 212 arranged radially inward extend along the full first circumference, whereas the fastener openings 210 which are radially outward extend along portions of the second circumference. For example, the lower support 202 may include one or more radially outward protrusions or flanges 208, each flange 208 including one or more of the aforementioned radially outward, fastener openings 210. In the present, non-limiting example, the lower support 202 includes three flanges 208, each comprising a plurality (e.g., six) fastener openings 210, wherein each flange 208 is generally configured to allow the attachment thereto of a respective one of the connectors 222 in such a way that the connector 222 can be selectively attached to one of the six available fastener openings 210. Alternatively, each connector 222 can be selectively attached to a radially-inward, fastener opening 212.

Figure 12:
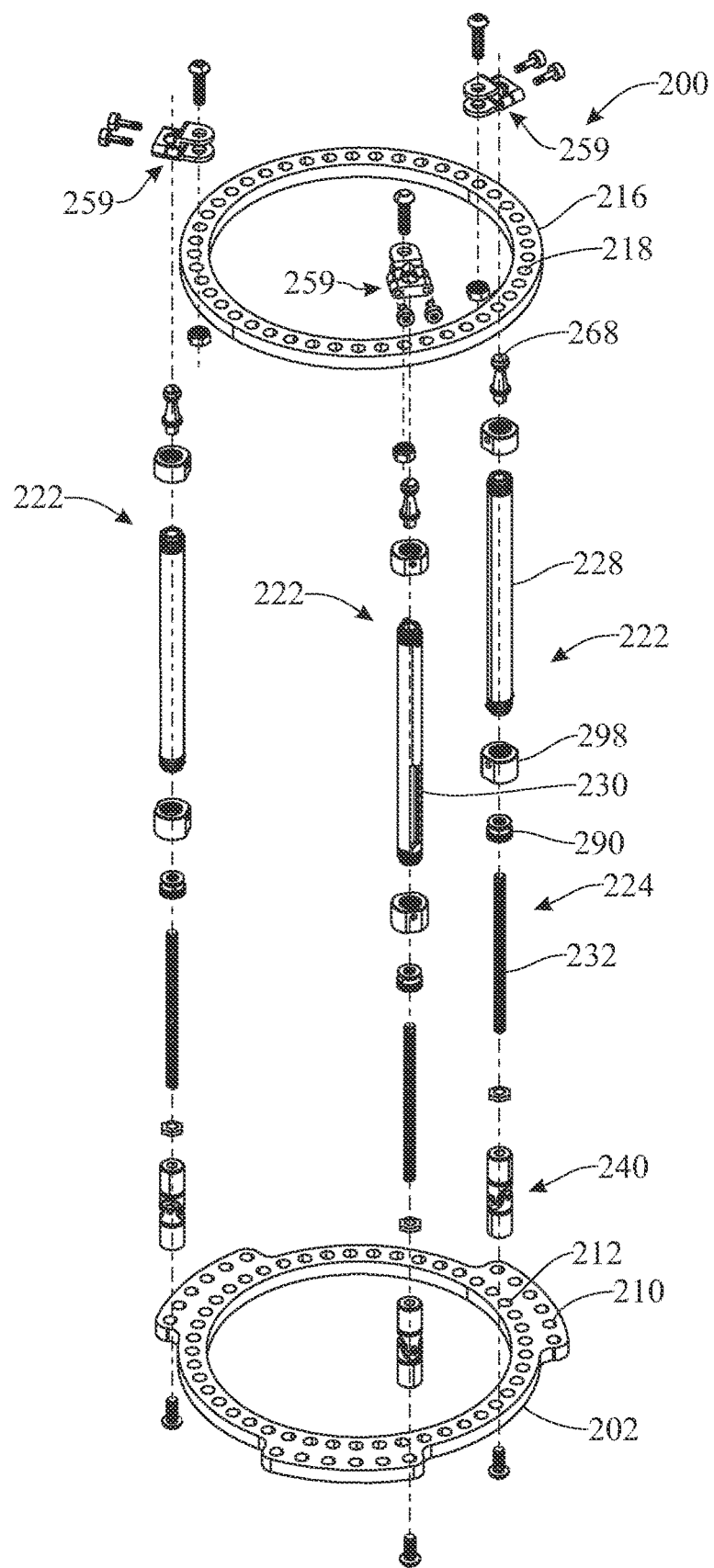
FIG. 12 presents an exploded top perspective view of the external fixation device of FIG. 10.
Figure 13:
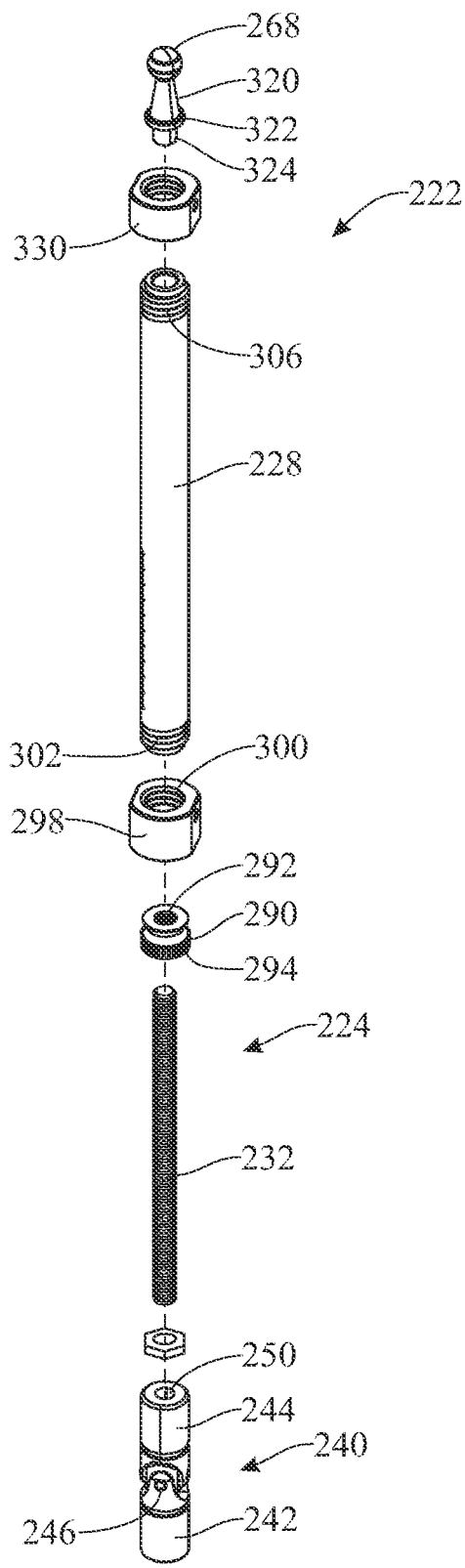
FIG. 13 presents an exploded top perspective view of one of the connectors of the external fixation device of FIG. 10.
Figure 17:
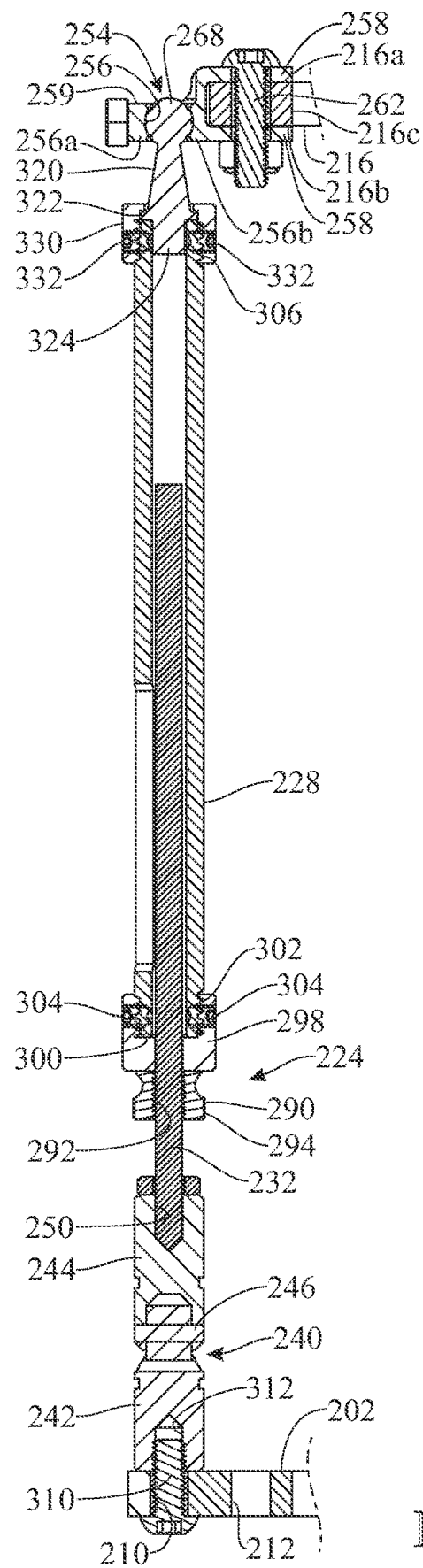
FIG. 17 presents a cross-sectional side elevation view, taken along section plane 17-17 indicated in FIG. 11, of a connector of the external fixation device of FIG. 10, with the upper support and the lower support disposed in axial alignment with each other and the plane of the lower support and the plane of the upper support parallel to each other.

As with the previous embodiment, each connector 222 may include one or more spacer assemblies to allow length adjustment of the connector 222. For instance, as best shown in FIGS. 12, 13 and 17, each connector 222 depicted herein specifically includes a single spacer assembly 224. The spacer assembly 224 comprises a threaded rod 232 and a sleeve 228, where the rod 232 is axially and rotationally movable within the sleeve 228, as best shown in FIG. 17.

The sleeve 228 includes a bottom threaded nut 290. The threaded nut 290 includes an interior thread 292 and an outer gripping surface 294 which may have a texture or finish which facilitates manually exerting a torque on the nut 290. The interior thread 292 of the nut 290 is configured to thread onto the rod 232. The nut 290 is attached to a bottom cap 298. The bottom cap 298 includes an interior thread 300 configured to thread onto a bottom threaded end 302 of the sleeve 228. As best shown in FIG. 17, one or more threaded fasteners 304 may be threaded radially inward through the bottom cap 298 and through the bottom threaded end 302 of the sleeve 228 and press against the rod 232 to prevent an axial relative movement between the rod 232 and the assembly formed by the sleeve 228, bottom cap 298 and threaded nut 290. In order to adjust the length of the connector 222, the threaded fasteners 304 are fist unthreaded sufficiently cease compression against the rod 232; next, the threaded nut 290 is turned relative to the rod 232 causing the aforementioned assembly to displace axially relative to the rod 232 and thereby extend or retract the rod 232 from or into the sleeve 228. Once the desired connector length is achieved, the threaded fasteners 304 are once more tightened against the rod 232 to prevent said axial displacement and secure the connector 222 at the desired length.

Figure 16:
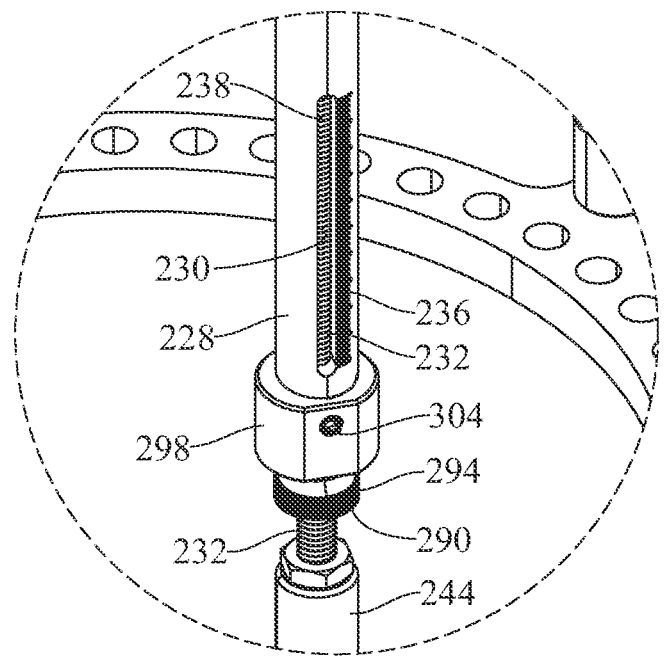
FIG. 16 presents a top perspective view of a bottom end of the sleeve and rod, showing an elongate slot and markings provided on the sleeve.

As best shown in FIG. 16, in some embodiments, an elongated slot 230 may be provided in the sleeve 228. Outer markings 236 may be included on the sleeve 228 to indicate a length adjustment value of the spacer assembly 224 or connector 222. For instance and without limitation, a mark 238 may be provided at a specific longitudinal position along the rod 232, wherein alignment of the mark 238 with a specific marking of the outer markings 236 indicates a length of the connector 222 or a degree of adjustment thereof).

Figure 19:
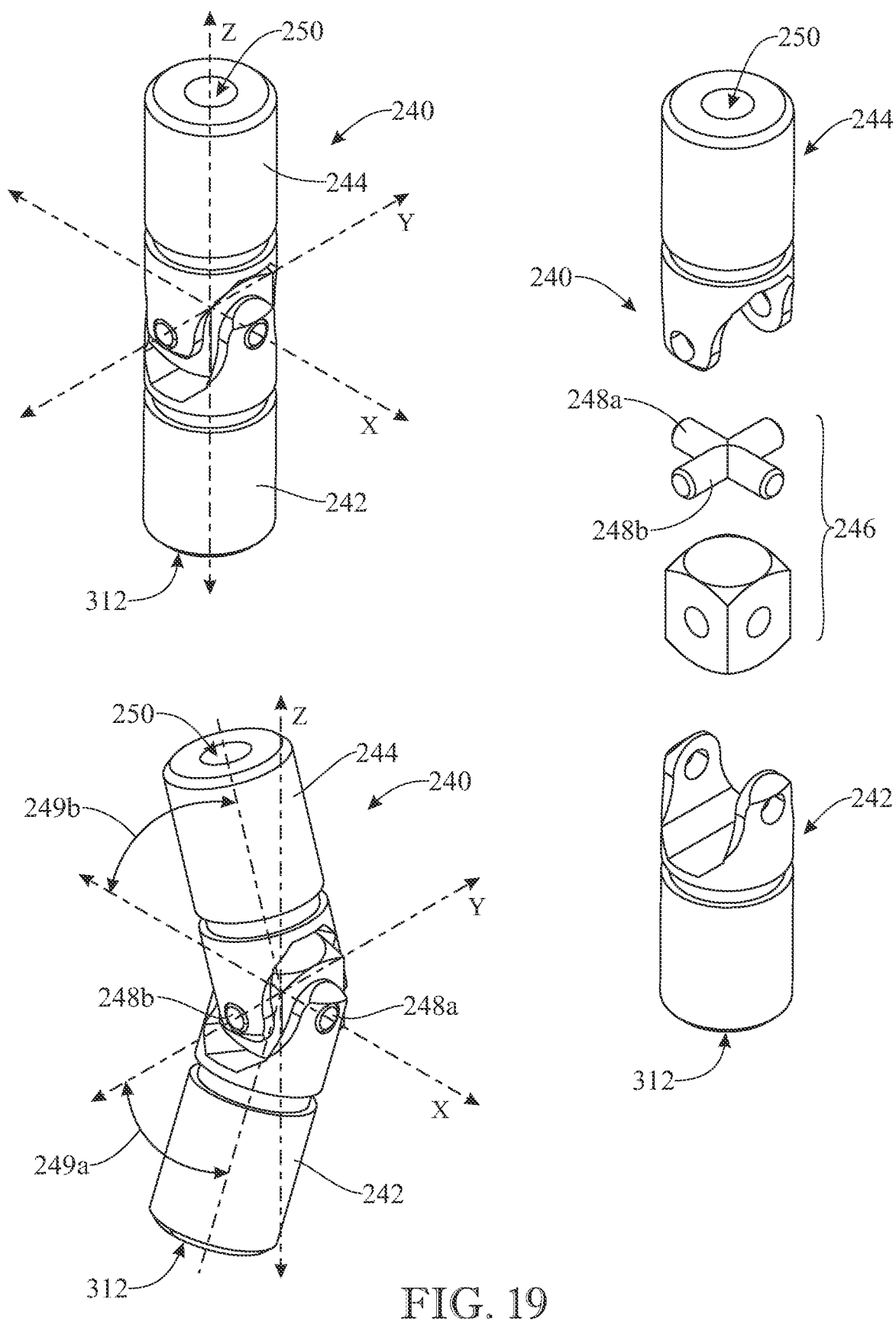
FIG. 19 presents an exploded view and first and second assembled views of the pivotal base joint, wherein the first assembled view shows the universal base joint in a straight configuration, and the second assembled view shows the universal base joint rotated about two cross shafts comprised therein.

As mentioned heretofore, the connectors 222 are pivotable relative to the lower support 202 by means of respective pivotal base joints 240. As best shown in the various views of FIG. 19, each pivotal base joint 240 may be formed as a universal joint including a lower joint component 242 and an upper joint component 244 articulately connected to one another by a cross shaft 246 comprising a first shaft 248a and a second shaft 248b which are perpendicular to one another. More specifically, the first shaft 248a may be formed along a first axis or x axis, and may provide a hinge for rotation of the lower joint component 242 about a rotation axis in the direction of axis x and thus along a plane comprising the y and z axes, as indicated by arrow 249a. In turn, the second shaft 248b may be formed along a second, perpendicular axis (the y axis), and may provide a hinge for rotation of the upper joint component 244 about a rotation axis in the direction of axis y and thus along a plane comprising the x and z axes, as indicated by arrow 249b. Therefore, the universal joint allows for freedom of rotation in multiple directions of the upper joint component 244 relative to the lower joint component 242.

Figure 11:
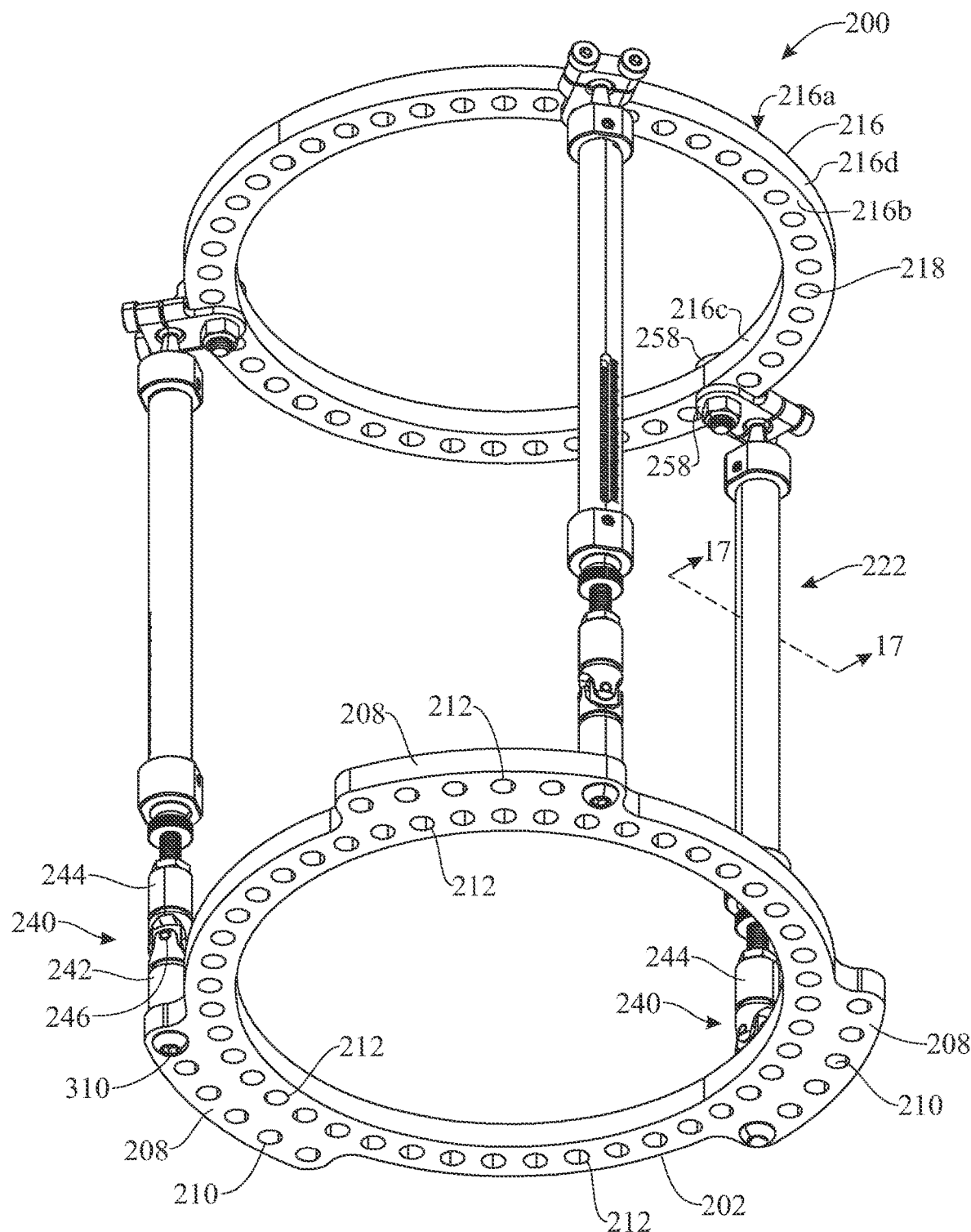
FIG. 11 presents a bottom perspective view of the external fixation device of FIG. 10, the external fixation device shown assembled.

The lower joint component 242 is preferably disconnectably attached to the lower support 202, such as by a threaded fastener 310. As best shown in FIGS. 11 and 17, the threaded fastener 310 may be inserted through (and optionally threaded to) one of the openings 212 or 210 of the lower support 202 and a bottom threaded opening 312 formed in the lower joint component 242. In turn, the upper joint component 244 is preferably disconnectably attached to the connector 222. For instance, as best shown in FIGS. 13 and 17, the connector 222 and upper joint component 244 may be disconnectably attached to one another by a threaded engagement between a second or bottom threaded end of the rod 232 and an interiorly-threaded opening 250 in the upper joint component 244.

Figure 14:
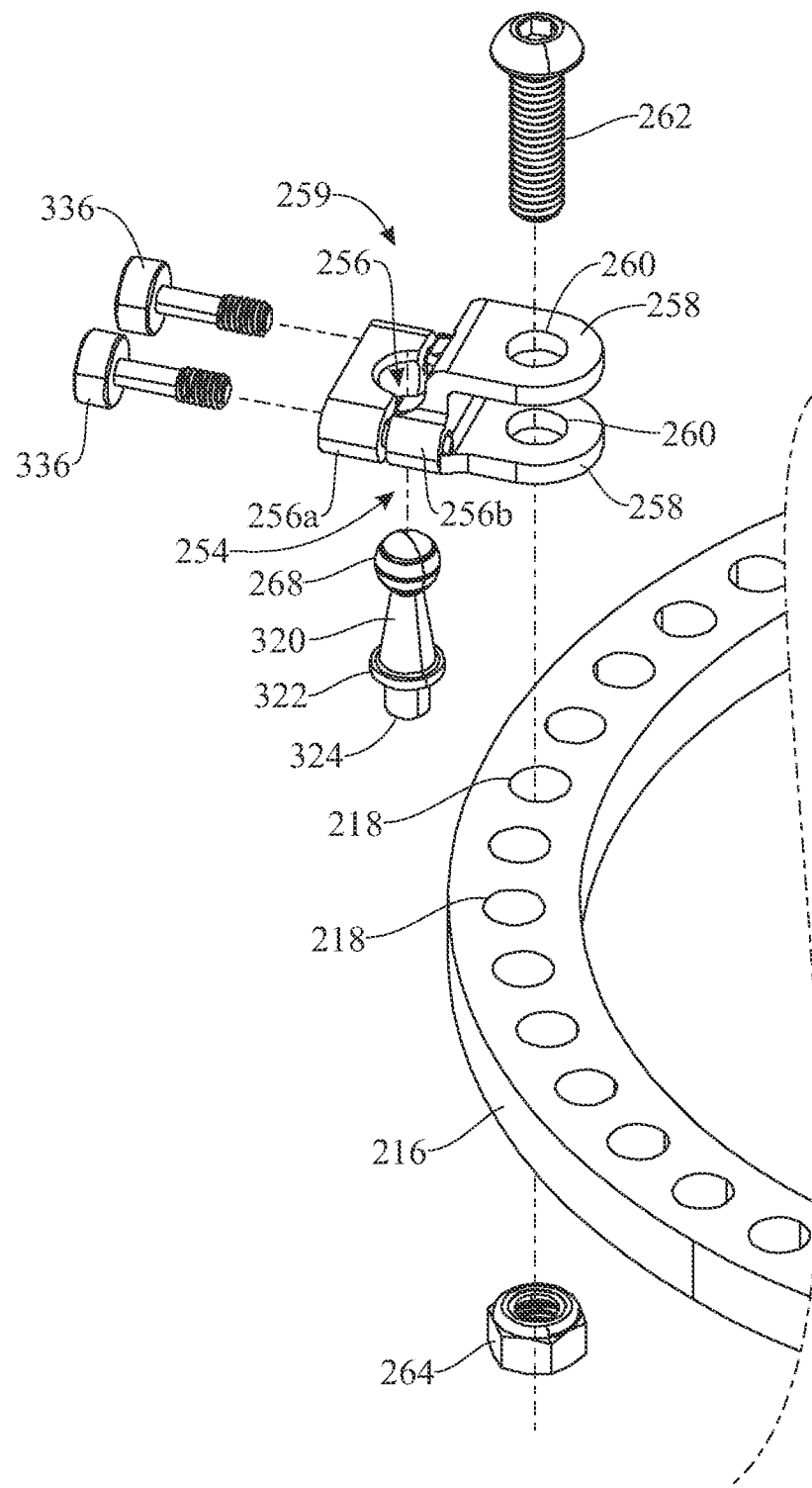
FIG. 14 presents an exploded top perspective view of a top area of one of the connectors and the upper support, showing details of a ball-and-socket joint.
Figure 15:
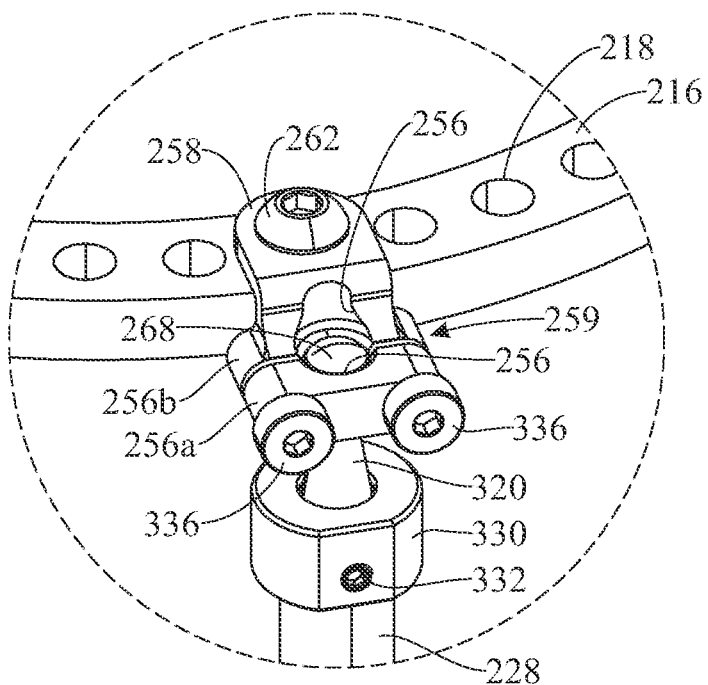
FIG. 15 presents a top perspective view of the top area of one of the connectors and the upper support, showing details of a ball-and-socket joint.

Similarly to the previous embodiment, and with reference now to FIGS. 13-15 and 17, each ball-and-socket joint 254 comprises a ball 268 and a socket 256 forming a ball-joint mechanism, wherein the ball 268 is carried by the connector 222 and the socket 256 is carried by the upper support 216. As best shown in FIG. 14, the ball 268 is integrally formed with a body 320 having a flange or shoulder 322 and a bottom end 324 extending from the shoulder 322 and having a smaller diameter than the shoulder 322. As shown in FIG. 17, the body 320 can be fitted onto the sleeve 228 such that the bottom end 324 of the body 320 is received inside the sleeve 228 and the shoulder 322 rests on a top end of the sleeve 228. A threaded, top cap 330 is fitted over the top end of the sleeve 228 and the shoulder 322 and threaded onto a top threaded end 306 of the sleeve 228 and retains the body 320—and ball 268—in place relative to the sleeve 228. As shown in FIGS. 15 and 17, one or more threaded fasteners 332 may be threaded radially inward through the top cap 330 and through the top end 306 of the sleeve 228 and press against the bottom end 324 of the body 320 to further prevent axial or rotational relative movement between the ball 268 and the assembly formed by the sleeve 228 and the top cap 330.

As mentioned heretofore, the socket 256 is carried by or associated to the upper support 216. For instance, as best shown in FIG. 4, at least one protruding arm or flange 258 (and more preferably, a pair of parallel, spaced-apart protruding arms or flanges 258 forming a clamp assembly configured to clamp over and onto opposite, outer sides of the second support 116 at different positions along the second support 116) may extend from the socket 256. More specifically, as shown for instance in FIGS. 10, 11 and 17, the upper support 216 includes an outer, top side 216a, an outer, bottom side 216b arranged opposite to the top side 216a and facing the lower support 202, an inner lateral side 216c, and an outer lateral side 216d; the pair of flanges 258 of the present embodiment are mounted over and onto the opposite, outer, top and bottom sides 216a and 216b of the upper support 216.

The flange or flanges 258 may include a respective fastener opening 260. A threaded, clamp fastener 262 may extend the fastener opening(s) 260 in the flange(s) 258 and through a selected one of the plurality of fastener openings 218 in the upper support 216, and a securing nut 264 may be threaded on the clamp fastener 262 to attach the flange(s) 258, and therefore the socket 256, to the upper support 216. In some embodiments, the socket 256 may be provided by a first socket portion 256a and a second socket portion 256b which can be adjustably secured to one another by one or more threaded, socket fasteners 336 allowing to selectively adjust the size of the socket 256 and to thereby loosen or tighten the ball-and-socket joint 254. As shown, when connected to the first and second socket portions 256a, 256b, the socket fasteners 336 may extend in a generally radial direction relative to a center of the upper support 216; more specifically, the socket fasteners 336 may extend radially inward, as shown, facilitating operation of the socket fasteners 336 from outside the upper support 216. Sufficient threading or unthreading of the threaded, socket fasteners 336 into the first and second socket portions 256a and 256b may respectively free the ball 268 from the socket 256, or prevent rotation of the ball 268 within the socket 256. As shown, the flanges 258 and socket 256 (i.e. the flanges 258 and first and second socket portions 256a and 256b) form a connecting member 259, or connector, which interfaces between the connector 222 and the upper support 216 to articulately connect one to the other at different selectable positions along the upper support 216. As further shown, when fastened, the socket fasteners 336 may be arranged at opposite sides of the socket 256, thereby contributing to maintain all sides of the socket 256 equally tightened and to increase compactness of the connecting member 259.

Figure 18:
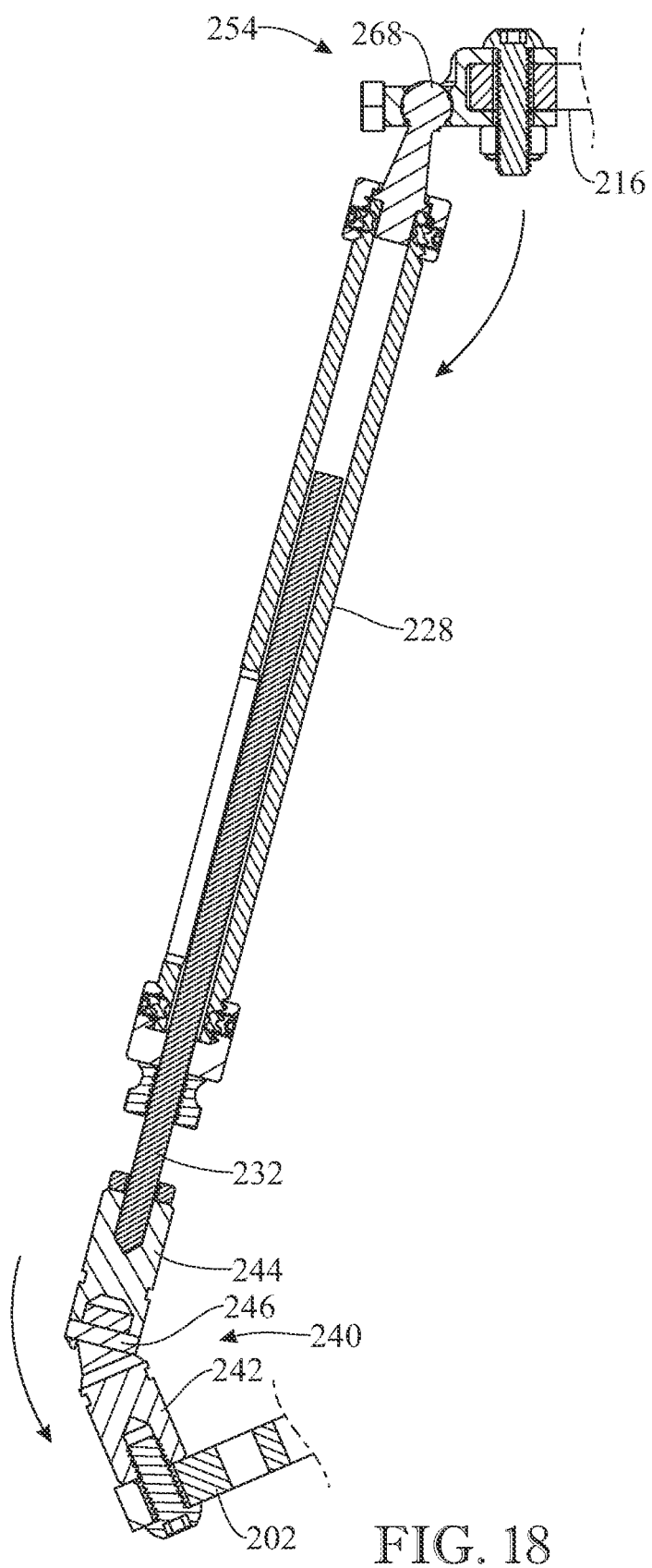
FIG. 18 presents a cross-sectional side elevation view of the connector of FIG. 17, with the upper support and the lower support disposed in axial misalignment with each other and the plane of the lower support and the plane of the upper support in angular relationship to each other.
Figure 20:
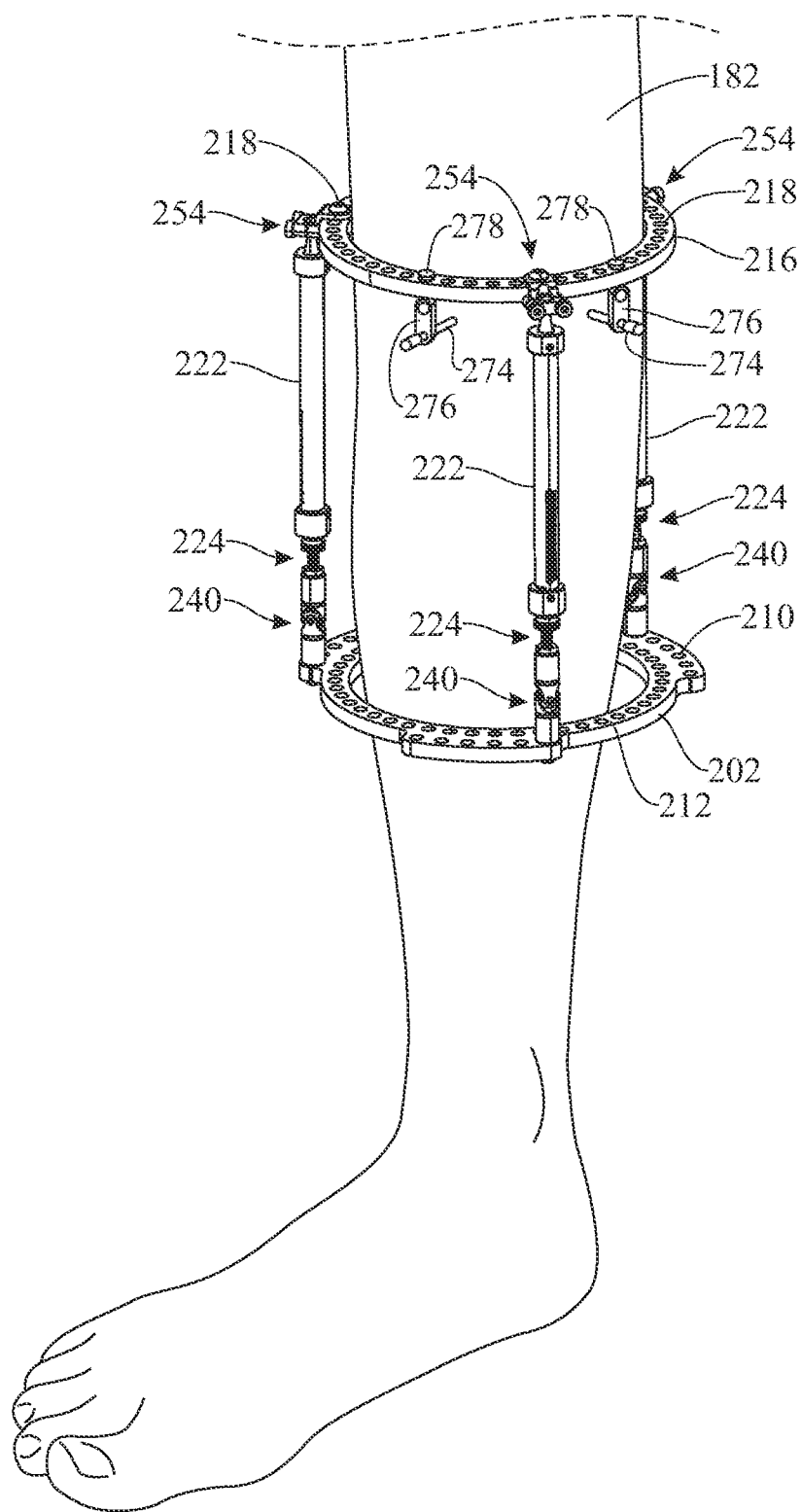
FIG. 20 presents a top perspective view of the external fixation device of FIG. 10 deployed in place on the leg of a patient in an illustrative application of the external fixation device.

Referring next to FIG. 20, as shown, the external fixation device 200 of the present embodiment may be installed in the leg 182 of a patient similarly to the installation described with reference to FIG. 9 and the external fixation device 100 of the first embodiment. More specifically, fixation bolts 274 may be threaded into the drilled holes and extended out from the leg 182 of the patient. The lower support 202 and/or the upper support 216 may be attached to the fixation bolts 274 using fixation bolt brackets 276. Mount fasteners 278 may be extended through the fastener openings 212 of the lower support 202 and/or the fastener openings 218 of the upper support 216 to secure the fixation bolt brackets 276 to the corresponding lower support 202 or upper support 216. The elongated links or connectors 222 may be individually adjusted in length as described heretofore. Adjustments may be made to the ball-and-socket joints 254 and the pivotal base joints 240 to ensure that the bone is aligned properly with little, if any, shortening of the bone. As illustrated in FIGS. 17 and 18, relative orientation of the lower support 202 and the upper support 216 may be selectively adjusted to different angles by adequately pivoting the ball-and-socket joints 254 and the pivotal base joints 240. Furthermore, as described heretofore, the lower support 202 can be connected to the connectors 222 at any of the fastener openings 212 or 210, and the upper support 216 can be attached to the connectors 222 at any of the fastener openings 218. Similarly, the fixation brackets 276 may be connected to the upper support 216 or lower support 202 at any of the fastener openings 218 or fastener openings 212 and 210, respectively, to adjustably position the fixation bolts 274 in dependence of the specific position of the fracture site. Thus, similarly to the first embodiment, the external fixation device 200 of the present embodiment can be rapidly and easily installed, and allows for multiple adjustments during treatment.

Figure 21:
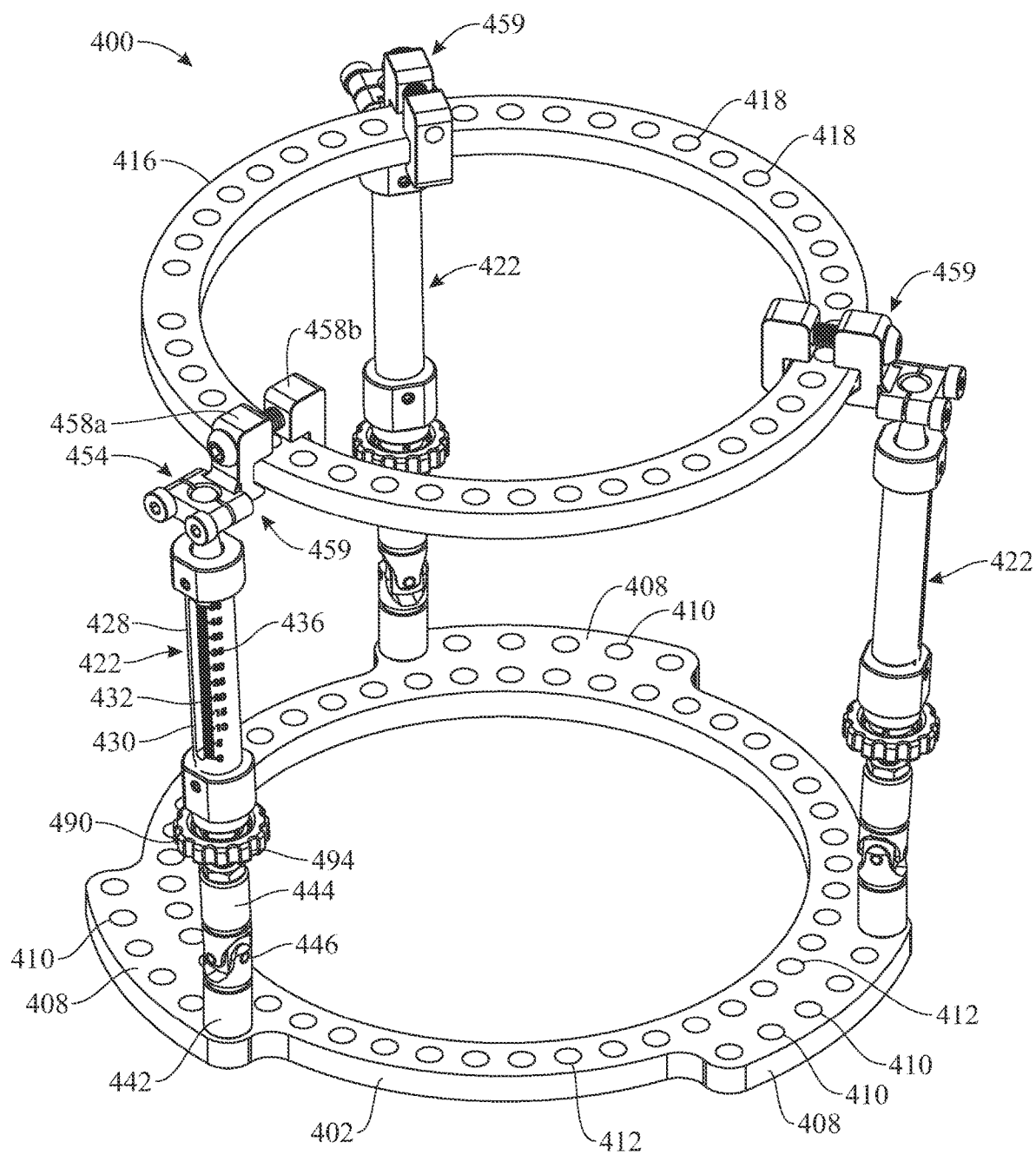
FIG. 21 presents a top perspective view of an external fixation device in accordance with a third illustrative embodiment of the present invention, the external fixation device shown assembled and including three connectors extending between annular tipper and lower supports.
Figure 22:
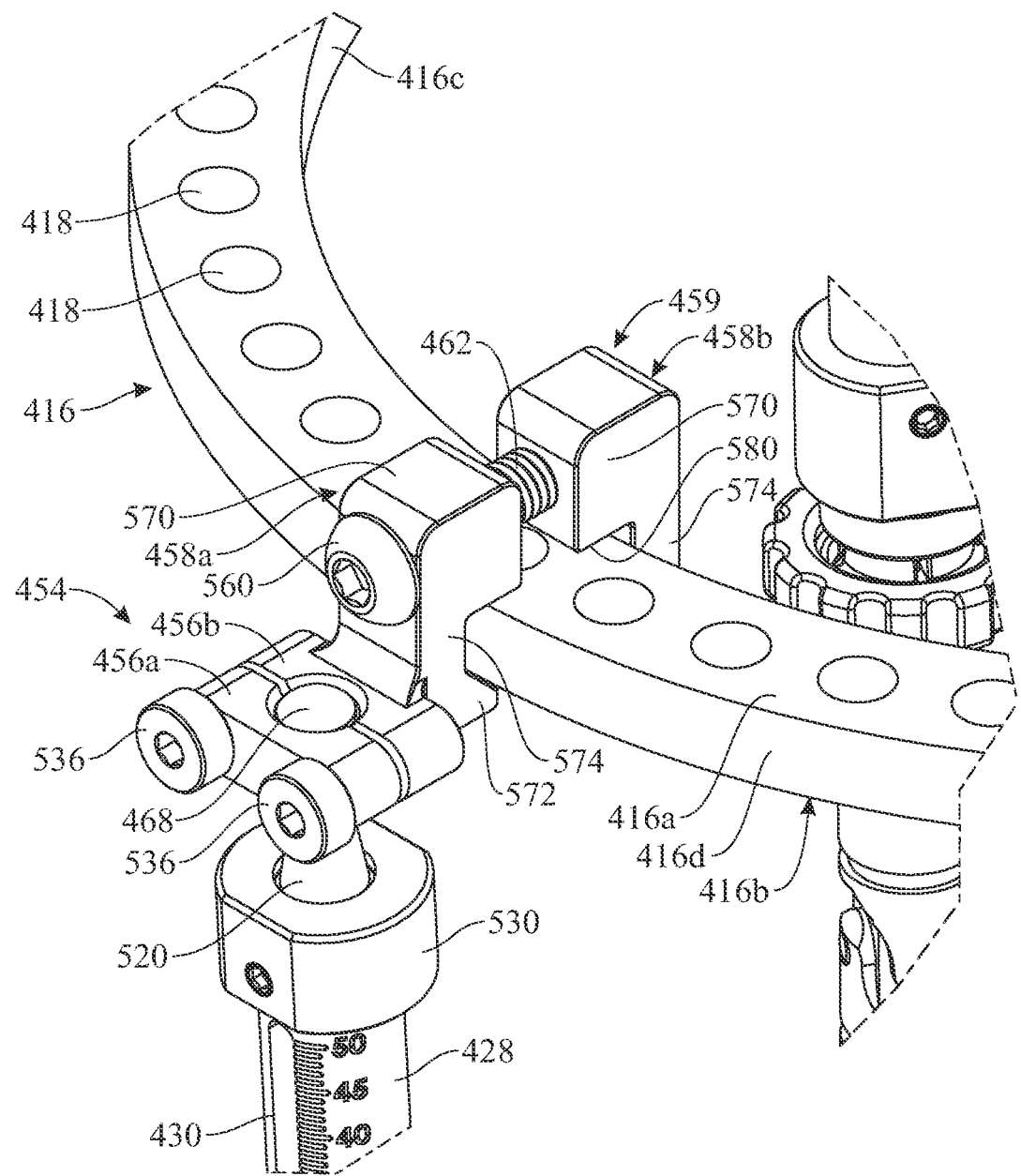
FIG. 22 presents an enlarged, top perspective view of an area of the external fixation device of FIG. 21 where a connecting member pivotably secures a connector to the upper support.
Figure 23:
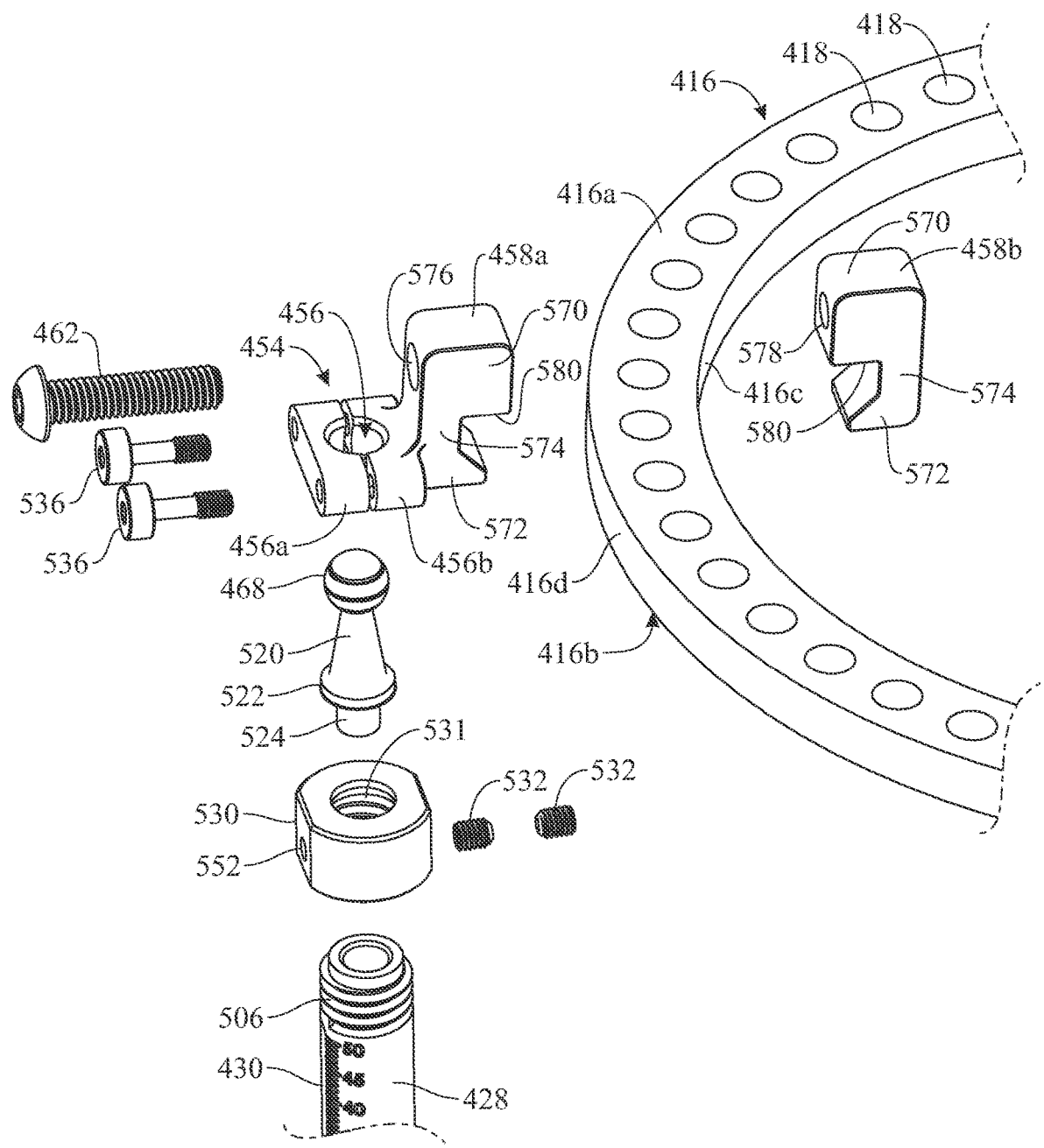
FIG. 23 presents another enlarged, top perspective view of the area depicted in FIG. 22, showing parts separated or exploded.

The illustrations of FIGS. 21-23 show an external fixation device 400 in accordance with a further embodiment of the invention. With reference initially to FIG. 21, similarly to the previous embodiments, the external fixation device 400 of the present embodiment includes a first or lower support 402 and a second or upper support 416 in spaced-apart relationship with one another, and one or more elongated links or connectors 422 connecting the upper support 416 to the lower support 402. More specifically, as in the previous embodiment, a plurality of connectors 422, such as, but not limited to, three connectors 422, may connect the tipper support 416 to the lower support 402. Also similarly to previous embodiments, each connector 422 is elongated, length-adjustable, and generally rigid to torsion. The various components of the external fixation device 400 may be fabricated of metal, plastic such as, but not limited to, DELRIN® plastic, composites, or combinations thereof, for instance and without limitation.

As shown in FIG. 21, the lower support 402 and the upper support 416 may be formed as closed-looped bodies, which may be annular or ring-shaped. A plurality of spaced-apart fastener openings 418 may extend through the upper support 416. In turn, the lower support 402 includes a plurality of spaced-apart fastener openings 412 arranged in discrete positions along a first circumference having a first radius about a center of the annular lower support 402, and a second plurality of spaced-apart fastener openings 410 arranged in discrete positions along a second circumference concentric to the first circumference and having a second radius lager than the first radius. The fastener openings 418 in the upper support 416 may correspond in number and position to the fastener openings 412 in the lower support 402. The fastener openings 410, 412 and 418 may be interiorly threaded. In the present embodiment, the fastener openings 412 arranged radially inward extend along the full first circumference, whereas the fastener openings 410 which are radially outward extend along portions of the second circumference, along radially outward protrusions or flanges 408. A respective top end of each connector 422 may be selectively attached to one of the fastener openings 418 of the upper support 416, and a respective bottom end of each connector 422 may be selectively attached to one of the fastener openings 410, 412 of the lower support 402.

As with the previous embodiments, length-adjustability of each connector 422 may be provided by one or more spacer assemblies 424, such as a single spacer assembly 424, including a sleeve 428 and a threaded rod 432 which is axially movable within the sleeve 428 by rotating a bottom threaded nut 490, which may include an outer gripping surface 494 to facilitate rotating the threaded nut 490. The threaded rod 432 may be visible through an elongated slot 430 formed in the sleeve 428. Outer markings 436 may be provided on the sleeve 428 to indicate a length adjustment value of the spacer assembly 424 or connector 422 corresponding to a respective longitudinal position of the threaded rod 432 along the sleeve 428.

As in the previous embodiments, each connector 422 is preferably disconnectably attached to the lower support 402 and the tipper support 416 by a respective articulated connection, allowing to selectively adjust the lower and tipper support 402 and 416 at various orientations and distances relative to each other. More specifically, a pivotal base joint 440 such as, but not limited to, a universal joint, as shown, may be preferably disconnectably connected to the lower support 402 and articulately connect each connector 422 to the lower support 402; similarly to the previous embodiment, the universal joint may include a lower joint component 442, an upper joint component 444, and a cross shaft 446. In turn, a ball-and-socket joint 454 may connect each connector 422 to the upper support 416.

With reference to FIGS. 22 and 23, also similarly to the previous embodiment, each ball-and-socket joint 454 comprises a ball 468 and a socket 456 forming a ball-joint mechanism, wherein the ball 468 is carried by the connector 422 and the socket 456 is carried by the upper support 416. As best shown in FIG. 23, the ball 468 is integrally formed with a stem or body 520 having a flange or shoulder 522 and a bottom end 524 extending downward from the shoulder 522 and having a smaller diameter than the shoulder 522. Similarly to the previous embodiment, the body 520 can be fitted onto the sleeve 428 such that the bottom end 524 of the body 520 is received inside the sleeve 428 and the shoulder 522 rests on a top end of the sleeve 428. A threaded, top cap 530, comprising a female or inner thread 531, is fitted over the top end of the sleeve 428 and the shoulder 522 and threaded onto a top threaded end 506 of the sleeve 428 and retains the body 520—and ball 468—in place relative to the sleeve 428; in some embodiments, more specifically, one or more threaded fasteners 532 may thread radially inward into respective threaded openings 552 formed in the top cap 530, and may abut against the body 520 and/or extend over the shoulder 522, thereby preventing the body 520 from axially and/or rotationally moving relative to the sleeve 428 and thus retaining the body 520—and ball 468—in place relative to the sleeve 428.

Similarly to the previous embodiment, the socket 456 may be provided by a first socket portion 456a and a second socket portion 456b which are adjustably positionable relative to one another and may be adjustably secured to one another by one or more threaded, socket fasteners 536 allowing to selectively adjust the size of the socket 456 and to thereby loosen or tighten the ball-and-socket joint 454. As shown, similarly to the previous embodiment, when connected to the first and second socket portions 456a, 456b, the socket fasteners 536 may extend in a generally radial direction relative to a center of the upper support 416; the socket fasteners 536 may extend radially inward, as shown, facilitating operation of the socket fasteners 536 from outside the upper support 416. Sufficient threading or unthreading of the threaded, socket fasteners 536 into the first and second socket portions 456a and 456b may respectively free the ball 468 from the socket 456, or prevent rotation of the ball 468 within the socket 456. As further shown, when fastened, the socket fasteners 536 may be arranged at opposite sides of the socket 456, thereby contributing to maintain all sides of the socket 456 equally tightened and to increase compactness of the connecting member 459.

As mentioned heretofore, the socket 456 is carried by or associated to the upper support 416. For instance, as best shown in FIGS. 22 and 23, similarly to the previous embodiment, a pair of spaced-apart, clamping arms, consisting of a first clamping arm 458a and a second clamping arm 458b, may form a clamp assembly configured to clamp over and onto opposite, outer sides of the upper support 416, and to carry the socket 456 and secure the socket 456 to the upper support 416. As shown, the first and second clamping arms 458a and 458b and socket 456 form a connecting member 459, or connector, which interfaces between the connector 422 and the upper support 416 to articulately connect one to the other at different selectable positions along the upper support 416.

Similarly to the previous embodiment, the first clamping arm 458a is integrally formed into a single piece unit with the second socket portion 456b. However, unlike the previous embodiment, the second clamping arms 458b of the present embodiment is not integrally formed into a single-piece unit with the first clamping arm 458 (and second socket portion 456b) but is rather formed as a separate part or piece. A clamp fastener 462 is configured to adjustably interconnect the first and second clamping arms 458a and 458b to one another, allowing to vary the separation between the first and second clamping arms 458a and 458b and thereby loosen or tighten the first and second clamping arms 458a and 458b from or against the upper support 416, respectively. In some embodiments, such as the present embodiment, the clamp fastener 462 may be a threaded fastener.

In some embodiments, at least one of the first clamping arm 458a and the second clamping arm 458b may include a first end portion 570, a second end portion 572, and a connecting portion 574. The first and second end portions 570 and 572 may extend from the connecting portion 574 in spaced-apart relationship such that the first end portion 570, second end portion 572 and connecting portion 574 form a C-shaped arrangement, as shown, the C-shape configured to receive or clamp over a side of the upper support 416. For instance, in the present embodiment, the first clamping arm 458a and the second clamping arm 458b are both formed in accordance with such a C-shaped arrangement, and are configured to receive or clamp over opposite sides of the upper support 416. In some embodiments, such as the present embodiment, the first and second clamping arms 458a, 458b may have substantially same size and shape, such that the first and second clamping arms 458a, 458b mirror each other.

With reference to FIG. 22, the first and second clamping arms 458a and 458b are configured to mount onto respective outer and inner lateral sides 416d and 416c of the upper support 416. Preferably, as shown, the first end portion 570 of each one of the first and second clamping arms 458a, 458b extends partially over and along a top side 416a of the tipper support 416. Alternatively or, preferably, additionally, the second end portion 572 of each one of the first and second clamping arms 458a, 458b extends partially below and along a bottom side 416b of the upper support 416. An inner side 580 of the first and second clamping arms 458a, 458b may be shaped and sized such that said inner side 580 generally conforms to an outer contour of the upper support 416 along the outer lateral side 416d, inner lateral side 416c, top side 416a and/or bottom side 416b of the upper support 416, as shown, and more preferably, along all of said sides, to further stabilize the first and second clamping arms 458a, 458b against the tipper support 416.

In some embodiments, the clamp fastener 462 may specifically connect the first end portions 570 of the first and second clamping arms 458a and 458b to one another. For instance, the clamp fastener 462 depicted herein extends through a first opening 576 formed in the first end portion 570 of the first clamping arm 458a and into a second opening 578 formed in the first end portion 570 of the second clamping arm 458b, without engaging the second support 416 (unlike previous embodiments, wherein the clamp fastener extends through the second support); such configuration enables the connecting member 459 to be selectively attachable to virtually any position along the upper support 416, rather than to discrete positions as in the previous embodiments. In some embodiments, the first opening 576 may be non-threaded or smooth, facilitating an expedited insertion of the clamp fastener 462 therethrough. Alternatively or, preferably, additionally, the second opening 578 may be threaded and configured for the threading thereto of the threaded clamp fastener 462, thereby allowing the clamp fastener 462 to tighten the first and second clamping arms 458a and 458b towards one another and against the upper support 416 without the need for a nut, also contributing to a rapid tightening of the first and second clamping arms 458a and 458b. In some embodiments, such as the present embodiment, assembly is further facilitated by having the inner side 580 non-rotatably engage with the upper support 416, thereby maintaining the first and second clamping arms 458a and 458b non-rotational while the threaded clamp fastener 462 is rotated about its central longitudinal axis in order to thread into the second opening 578 of the second clamping arm 458b.

In some embodiments, the first end portion 570 of the first clamping arm 458a may be spaced-apart from the second socket portion 456b such that, when assembled onto the upper support 416, the first end portion 570 is arranged higher than the first and second socket portions 456a and 456b; for instance, the second socket portion 456b may be integrally formed with, and extend laterally (radially) outward from, the connecting portion 574 or the second end portion 572 of the first clamping arm 458a. As best shown in FIG. 22, such configuration allows the clamp fastener 462 to be arranged in spaced-apart relationship with the socket fasteners 536, facilitating selective independent operation of the different fasteners 462, 536. Furthermore, in preferred embodiments, such as the present embodiment, the fasteners 462, 536 may extend generally parallel to one another, such as in a generally radial direction, as shown, thereby allowing to more intuitively and rapidly thread or otherwise connect the fasteners 462, 536 during assembly; such rapid assembly may be enhanced by having all fasteners 462, 536 operable from a same side of the upper support 416 (from the outer side). Furthermore, the depicted embodiment advantageously maintains the ball-and-socket joint 454 vertically spaced apart (lower than) the upper support 416, thereby facilitating visibility of the upper support 416 from the side, and minimizing interference between the connector 422 and the upper support 416 when rotationally adjusting the ball-and-socket joint 454.

Alternative embodiments are contemplated to those shown in the drawings and/or described herein. For example, it is contemplated that the ball-and-socket joint may extend off the side of each connector rather than being disposed in axial alignment with the connector.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. An external fixation device for stabilizing fractured bones in the treatment of traumatic injuries, comprising:
   a first support configured to extend at least partially around a limb;
   a second support configured to extend at least partially around said limb;
   one or more connecting members, wherein each connecting member comprises a clamp assembly configured to selectively clamp over and onto opposite, outer sides of the second support at different positions along the second support; and
   one or more elongated links, wherein each elongated link is pivotably connectable to the first support by a first articulated connection and is pivotably connectable to a respective connecting member of the one or more connecting members by a second articulated connection, the second articulated connection comprising a ball-and-socket joint; wherein
   the external fixation device is configured to adopt an assembled configuration in which each elongated link of the one or more elongated links is connected to the first support at the first articulated connection and to the respective connecting member at the second articulated connection, and the clamp assembly of said respective connecting member is clamped over and onto opposite sides of the second support at a selected position of said different positions along the second support, with the ball-and-socket joint arranged radially outward of the second support with respect to a center of the second support, and further in which the elongated links extend between the first and second supports and maintain the first and second supports in a spaced-apart relationship with one another, and
   wherein the clamp assembly of said each connecting member comprises a first clamping arm and a second clamping arm, wherein, in the assembled configuration of the external fixation device, the first and second clamping arms are clamped over and onto said opposite sides of the second support, respectively, and wherein, in said assembled configuration of the external fixation device, the first clamping arm of the clamp assembly of said each connecting member is clamped over and onto an outer lateral side of the second support and the second clamping arm of the clamp assembly of said each connecting member is clamped over and onto an opposite, inner lateral side of the second support, the inner lateral side facing a center of the second support.

2. An external fixation device for stabilizing fractured bones in the treatment of traumatic injuries, comprising:
a first support configured to extend at least partially around a limb;
a second support configured to extend at least partially around said limb;
one or more connecting members, wherein each connecting member comprises a clamp assembly configured to selectively clamp over and onto opposite, outer sides of the second support at different positions along the second support; and
one or more elongated links, wherein each elongated link is pivotably connectable to the first support by a first articulated connection and is pivotably connectable to a respective connecting member of the one or more connecting members by a second articulated connection, the second articulated connection comprising a ball-and-socket joint; wherein
the external fixation device is configured to adopt an assembled configuration in which each elongated link of the one or more elongated links is connected to the first support at the first articulated connection and to the respective connecting member at the second articulated connection, and the clamp assembly of said respective connecting member is clamped over and onto opposite sides of the second support at a selected position of said different positions along the second support, with the ball-and-socket joint arranged radially outward of the second support with respect to a center of the second support, and further in which the elongated links extend between the first and second supports and maintain the first and second supports in a spaced-apart relationship with one another, and
wherein the clamp assembly of said each connecting member comprises a first clamping arm and a second clamping arm, wherein, in the assembled configuration of the external fixation device, the first and second clamping arms are clamped over and onto said opposite sides of the second support, respectively, and
wherein the first and second clamping arms are integrally formed with one another.

3. An external fixation device for stabilizing fractured bones in the treatment of traumatic injuries, comprising:
a first support configured to extend at least partially around a limb;
a second support configured to extend at least partially around said limb;
one or more connecting members, wherein each connecting member comprises a clamp assembly configured to selectively clamp over and onto opposite, outer sides of the second support at different positions along the second support; and
one or more elongated links, wherein each elongated link is pivotably connectable to the first support by a first articulated connection and is pivotably connectable to a respective connecting member of the one or more connecting members by a second articulated connection, the second articulated connection comprising a ball-and-socket joint; wherein
the external fixation device is configured to adopt an assembled configuration in which each elongated link of the one or more elongated links is connected to the first support at the first articulated connection and to the respective connecting member at the second articulated connection, and the clamp assembly of said respective connecting member is clamped over and onto opposite sides of the second support at a selected position of said different positions along the second support, with the ball-and-socket joint arranged radially outward of the second support with respect to a center of the second support, and further in which the elongated links extend between the first and second supports and maintain the first and second supports in a spaced-apart relationship with one another, and
wherein the clamp assembly of said each connecting member comprises a first clamping arm and a second clamping arm, wherein, in the assembled configuration of the external fixation device, the first and second clamping arms are clamped over and onto said opposite sides of the second support, respectively, and
wherein the second support comprises a plurality of openings formed therealong and defining said different positions, and further wherein the clamp assembly of said each connecting member further comprises a clamp fastener extendable through respective openings formed in the first and second clamping arms, wherein, in the assembled configuration of the external fixation device, the clamp fastener extends through the openings of the first and second clamping arms of the clamp assembly of said each connecting member and through a selected opening of the plurality of openings of the second support and secures the clamp assembly of said each connecting member to the second support at said selected position.

4. An external fixation device for stabilizing fractured bones in the treatment of traumatic injuries, comprising:
a first support configured to extend at least partially around a limb;
a second support configured to extend at least partially around said limb;
one or more connecting members, wherein each connecting member comprises a clamp assembly configured to selectively clamp over and onto opposite, outer sides of the second support at different positions along the second support; and
one or more elongated links, wherein each elongated link is pivotably connectable to the first support by a first articulated connection and is pivotably connectable to a respective connecting member of the one or more connecting members by a second articulated connection, the second articulated connection comprising a ball-and-socket joint; wherein
the external fixation device is configured to adopt an assembled configuration in which each elongated link of the one or more elongated links is connected to the first support at the first articulated connection and to the respective connecting member at the second articulated connection, and the clamp assembly of said respective connecting member is clamped over and onto opposite sides of the second support at a selected position of said different positions along the second support, with the ball-and-socket joint arranged radially outward of the second support with respect to a center of the second support, and further in which the elongated links extend between the first and second supports and maintain the first and second supports in a spaced-apart relationship with one another, and wherein the clamp assembly of said each connecting member comprises a first clamping arm and a second clamping arm, wherein, in the assembled configuration of the external fixation device, the first and second clamping arms are clamped over and onto said opposite sides of the second support, respectively, and wherein the clamp assembly of said each connecting member further comprises a clamp fastener connectable to respective openings formed in the first and second clamping arms, wherein, in the assembled configuration of the external fixation device, the clamp fastener connects to the openings of the first and second clamping arms of the clamp assembly of said each connecting member without engaging the second support, the clamp fastener adjusting the first and second clamping arms against the second support to secure the clamp assembly of said each connecting member to the second support at said selected position.

5. An external fixation device for stabilizing fractured bones in the treatment of traumatic injuries, comprising:
 a first support configured to extend at least partially around a limb;
 a second support configured to extend at least partially around said limb;
 one or more connecting members, wherein each connecting member comprises a clamp assembly configured to selectively clamp over and onto opposite, outer sides of the second support at different positions along the second support; and
 one or more elongated links, wherein each elongated link is pivotably connectable to the first support by a first articulated connection and is pivotably connectable to a respective connecting member of the one or more connecting members by a second articulated connection, the second articulated connection comprising a ball-and-socket joint; wherein
 the external fixation device is configured to adopt an assembled configuration in which each elongated link of the one or more elongated links is connected to the first support at the first articulated connection and to the respective connecting member at the second articulated connection, and the clamp assembly of said respective connecting member is clamped over and onto opposite sides of the second support at a selected position of said different positions along the second support, with the ball-and-socket joint arranged radially outward of the second support with respect to a center of the second support, and further in which the elongated links extend between the first and second supports and maintain the first and second supports in a spaced-apart relationship with one another, and wherein the clamp assembly of said each connecting member comprises a first clamping arm and a second clamping arm, wherein, in the assembled configuration of the external fixation device, the first and second clamping arms are clamped over and onto said opposite sides of the second support, respectively, and wherein at least one of the first and second clamping arms is integrally formed with and extends from a portion of the ball-and-socket joint comprised in the clamp assembly of said each connecting member, and wherein the clamp assembly of said each connecting member further comprises first and second socket portions, the first and second socket portions adjustably securable at different distances relative to one another to vary a size of the socket, wherein said portion of the ball-and-socket joint is provided by the second socket portion, and wherein the clamp assembly of said each connecting member further comprises at least one socket fastener configured to secure the first and second socket portions at said different distances relative to one another, and wherein the clamp assembly of said each connecting member further comprises a clamp fastener connectable to respective openings formed in the first and second clamping arms, wherein, in the assembled configuration of the external fixation device, the clamp fastener is arranged generally parallel to the at least one socket fastener and connects to the openings of the first and second clamping arms of the clamp assembly of said each connecting member without engaging the second support, the clamp fastener adjusting the first and second clamping arms against the second support and thereby securing the clamp assembly of said each connecting member to the second support at said selected position.

* * * * *